US005814328A

United States Patent [19]
Gunasekaran

[11] Patent Number: 5,814,328
[45] Date of Patent: Sep. 29, 1998

[54] PREPARATION OF COLLAGEN USING PAPAIN AND A REDUCING AGENT

[76] Inventor: Subramanian Gunasekaran, 5686 Geranium Ct., Newark, Calif. 94560

[21] Appl. No.: 782,138

[22] Filed: Jan. 13, 1997

[51] Int. Cl.$^6$ .............................. A61F 2/00; A61K 38/17; C12P 21/06; C07K 1/14
[52] U.S. Cl. ......................... 424/426; 424/548; 435/68.1; 435/267; 514/21; 530/356; 530/402; 530/412
[58] Field of Search .................................. 435/68.1, 267; 530/356, 402, 412; 424/426, 548; 514/21

[56] References Cited

U.S. PATENT DOCUMENTS

| | | | |
|---|---|---|---|
| 2,202,566 | 5/1940 | Schulte | 18/54 |
| 3,113,568 | 12/1963 | Robins | 128/156 |
| 3,157,524 | 11/1964 | Artandi | 106/122 |
| 3,491,760 | 1/1970 | Braun et al. | 128/334 |
| 3,529,530 | 9/1970 | Tsuzuki | 99/18 |
| 3,664,844 | 5/1972 | Miller | 99/18 |
| 3,800,792 | 4/1974 | McKnight et al. | 128/156 |
| 4,148,664 | 4/1979 | Cruz, Jr. | 106/161 |
| 4,350,629 | 9/1982 | Yannas et al. | 260/123.7 |
| 4,407,787 | 10/1983 | Stemberger | 424/28 |
| 4,409,332 | 10/1983 | Jeffries et al. | 435/188 |
| 4,412,947 | 11/1983 | Cioca | 260/123.7 |
| 4,424,208 | 1/1984 | Wallace et al. | 424/177 |
| 4,485,095 | 11/1984 | Fujisaki et al. | |
| 4,485,097 | 11/1984 | Bell | |
| 4,488,911 | 12/1984 | Luck et al. | 106/161 |
| 4,511,653 | 4/1985 | Play et al. | 435/69 |
| 4,539,716 | 9/1985 | Bell | 623/1 |
| 4,546,500 | 10/1985 | Bell | 623/1 |
| 4,557,764 | 12/1985 | Chu | 106/161 |
| 4,597,762 | 7/1986 | Walter et al. | 623/1 |
| 4,600,533 | 7/1986 | Chu | 530/356 |
| 4,604,346 | 8/1986 | Bell et al. | |
| 4,655,980 | 4/1987 | Chu | 264/102 |
| 4,687,518 | 8/1987 | Miyata et al. | 106/161 |
| 4,689,399 | 8/1987 | Chu | 530/356 |
| 4,703,108 | 10/1987 | Silver et al. | 530/356 |
| 4,725,671 | 2/1988 | Chu et al. | 530/356 |
| 4,772,288 | 9/1988 | Borner et al. | 8/94.11 |
| 4,789,401 | 12/1988 | Ebinger et al. | 106/122 |
| 4,835,102 | 5/1989 | Bell et al. | 435/29 |
| 4,837,379 | 6/1989 | Weinberg | 424/101 |
| 4,841,962 | 6/1989 | Berg et al. | 128/156 |
| 4,883,864 | 11/1989 | Scholz | 530/356 |
| 4,894,441 | 1/1990 | Menicagli | 530/356 |
| 4,931,546 | 6/1990 | Tardy et al. | 530/356 |
| 4,948,540 | 8/1990 | Nigam | 264/28 |
| 4,950,483 | 8/1990 | Ksander et al. | 424/422 |
| 4,969,912 | 11/1990 | Kelman et al. | 623/66 |
| 4,975,527 | 12/1990 | Koezuka et al. | 530/356 |
| 5,002,071 | 3/1991 | Harrell | 128/897 |

(List continued on next page.)

OTHER PUBLICATIONS

Junqueira and Carneiro, *Basic Histology*, 4th ed., Lange Medical Publications, Los Altos, CA, (1983), pp. 89–119.
Prudden, "Wound Healing Produced by Cartilage Preparations," *Arch. Surg.* 89:1046–1059 [1964].
Peacock et al., "Use of Tanned Collagen Sponges in the Treatment of Liver Injuries," *Ann. Surg.* 161:238–247 [1965].
Beachey et al., "Collagen–Platelet Interaction," in *International Review of Connective Tissues*, (Eds. Chvapil et al.) Academic Press, 6:1–55 [1979].
Smith and Kimmel, "Papain (with a Section on Ficin)," in *The Enzymes*, vol. 4, 2d ed., (Eds. Boyer et al.) Academic Press, NY, p. 138 [1960].
Coulson, "The Effect of Proteolytic Enzymes on the Tensile Strength of Whole Aorta and Isolated Aortic Elastin," *Biochim. Biophys. Acta* 237:378–385 [1971].
Smith et al., "Pharmacology: Enzyme Dissolution of the Nucleus Pulposus," *Nature* 198:1311–1312 [1963].
Nimni et al., "Bioprosthesis derived from crosslinked and chemically modified collagenous tissues," in *Collagen*, vol. 3, (Eds. M.E. Nimni et al.) CRC Press, Inc., Boca Raton, FL [1988], pp. 1–39.
Amiel et al., "Biochemistry of tendon and ligament," in *Collagen*, vol. 3, pp. 223–229.
Soskel et al., "Isolation and Characterization of Insoluble and Soluble Elastins," *Meth. Enzymol.* 144:196–215 [1952].
Hill and Harper, "Quantitation of Types I and III Collagens in Human Tissue Samples and Cell Culture by Cyanogen Bromide Peptide Analysis," *Anal. Biochem.* 141:83–93 [1984].
Folch et al., "A Simple Method for The Isolation and Purification of Total Lipides From Animal Tissues," *J. Biol. Chem.* 226:497–509 [1957].
Skipski et al., "Quantitative Analysis of Phospholipids by Thin–Layer Chromatography," *Biochem. J.* 90:374–378 [1964].
Rouser et al., "Quantitative Analysis of Brain and Spinach Leaf Lipids Employing Silicic Acid Column Chromatography and Acetone for Elution of Glycolipids," *Lipids* 2:37–40 [1967].

(List continued on next page.)

Primary Examiner—David M. Naff
Attorney, Agent, or Firm—Medlen & Carroll, LLP

[57] ABSTRACT

Purified collagen is produced by contacting a collagen sample with a first proteolytic enzyme, a reducing agent and a second proteolytic enzyme. Preferably, the first and second proteolytic enzymes are papain and the reducing agent is sodium sulfide, dithiothreitol, glutathionine or sodium borohydride. The purified collagen may be contacted with a delipidation agent such as chloroform or methanol and with a phosphorylation agent such as sodium trimetaphosphate to form a biocompatible collagen. Prior to phosphorylation, the delipidated collagen may be treated by compressing, dehydrating, dispersing and drying to form collagen fibers. Also, prior to phosphorylation, the delipidated collagen may be subjected to filter-sterilizing. De-epithelializing of the collagen may carried out prior to treating with the first proteolytic enzyme. The purified and biocompatible collagen may be used in transplantation or hemostasis, and may be provided with compounds such as antimicrobials, antivirals, growth factors and other compounds suitable for biomedical use.

16 Claims, 2 Drawing Sheets

U.S. PATENT DOCUMENTS

| | | | |
|---|---|---|---|
| 5,028,597 | 7/1991 | Kodama et al. | 514/56 |
| 5,028,695 | 7/1991 | Eckmayer et al. | 530/356 |
| 5,043,426 | 8/1991 | Goldstein | 530/356 |
| 5,064,941 | 11/1991 | Davison . | |
| 5,081,106 | 1/1992 | Bentley et al. | 514/5 |
| 5,104,660 | 4/1992 | Chvapil et al. | 424/445 |
| 5,104,957 | 4/1992 | Kelman et al. . | |
| 5,106,949 | 4/1992 | Kemp et al. | 530/356 |
| 5,116,389 | 5/1992 | Mitz | 8/127.5 |
| 5,162,506 | 11/1992 | Hadden | 530/412 |
| 5,229,497 | 7/1993 | Boni | 530/356 |
| 5,316,942 | 5/1994 | Fink | 435/273 |
| 5,332,802 | 7/1994 | Kelman et al. | 530/356 |
| 5,374,539 | 12/1994 | Nimni et al. | 435/68.1 |
| 5,383,930 | 1/1995 | Brannan et al. | 623/11 |

OTHER PUBLICATIONS

Stegeman, "Mikrobestimmung von Hydroxyprolin mit Chloramin–T und p–Dimethylaminobenzaldehyd," *J. Physiol. Chem.* 311:41–45 [1958].

Blumenkrantz and Absoe–Hansen,"An Assay for total Hexosamine and a Differential Assay for Glucosamine and Galactosamine," *Clin. Biochem.* 9:269–274 [1976].

Fiske and Subbarow, "The Colorimetric determination of Phosphorus," *J. Biol. Chem.* 66:375–400 [1925].

Bradenberger and Hanson, "Eine spektrophotometrische Bestimmungsmethode für sauer und alkalische Phosphatasen," *Helv. Chim. Acta* 36:900–907 [1953].

Hofstee, "Direct and Continuous Spectrophotometric Assay of Phosphomonoesterases," *Arch. Biochem. Biophys.* 51:139–146 [1954].

Gunasekaran et al., "Collagen/ Phospholipid Interaction: Possible role in Skin Wound Dressings," *Proc. Soc. Biomater.* 20:311 [1994].

Simmons et al., "Corneal Epithelial Wound Closure in Tissue Culture: An in Vitro Model of Ocular Irritancy," *Toxicol. Appl. Pharmacol.* 88:13–23 [1987].

Jumblatt and Neufeld, "A Tissue Culture Assay of Corneal Epithelial Wound Closure," *Invest. Ophthamol. Visual Sci.* 15:8–13 [1986].

Gunasekaran, "Collagen–Based Wound Dressings: How to Control Infection and Immune Response," in *Encyclopedia of Biomaterials and Bioengineering*, 2(37);1267–1284 [1995].

Brown, *Hematology: Principles and Practice*, 3d ed., Eds. Lea & Febiger, Philadelphia, (1980), pp. 125–126.

Structure of Serine Side Chain (A)

Structure of Tri sodium metaphosphate:

(B)

REACTION:

PREPARATION OF COLLAGEN USING PAPAIN AND A REDUCING AGENT

FIELD OF THE INVENTION

The present invention relates to methods for preparing collagen from tissues of humans and other animals. In particular, the present invention provides methods for the preparation of collagen suitable for biomedical, veterinary, and other applications.

BACKGROUND OF THE INVENTION

Collagen is the most abundant protein in mammals. (See, U.S. Pat. No. 5,043,426 to Goldstein, herein incorporated by reference). Indeed, it represents 30% of the dry weight of the human body. (See, L. C. Junqueira and J. Carneiro, *Basic Histology*, 4th ed., Lange Medical Publications, Los Altos, CA, [1983], pp. 89–119). Vertebrate collagen is actually a family of proteins produced by several cell types. Within this protein family, the collagen types are distinguishable by their chemical compositions, different morphological and pathological features, distributions within tissues, and their functions. Although many types of collagen have been described, five major types have been recognized.

A. Forms Of Collagen

Collagen type I is the most abundant form of collagen, with widespread distribution within the body. It is present in tissues in structures classically referred to as "collagen fibers" that form bones, dentin, tendons, fascias, sclera, organ capsules, dermis, fibrous cartilage, etc. The primary function of type I collagen is to resist tension. Microscopically, type I collagen appears as closely packed, thick, non-argyrophilic, strongly birefringent red or yellow fibers. Its ultrastructure is characterized as being densely packed, thick fibrils with marked variation in diameter. It is produced by fibroblasts, osteoblasts, odontoblasts, and chondroblasts.

Collagen type II is primarily found in cartilage (e.g., hyaline and elastic cartilages). The primary function of type II collagen is to resist intermittent pressure. Microscopically, it appears as a loose, collagenous network, that is visible only with picrosirius stain and polarization microscopy. Ultrastructurally, it is characterized as appearing to have no fibers, but with very thin fibrils embedded in abundant ground substance. It is produced by chondroblasts.

Collagen type III is commonly associated with type I collagen in tissues, and may be the collagenous component of reticular fibers. It is present in smooth muscles, endoneurium, arteries, uterus, liver, spleen, kidney, an lung tissue. The primary function of type III collagen is to maintain the structure of expansible organs. Microscopically, it appears as a loose network of thin, argyrophilic, and weakly birefringent greenish fibers. Ultrastructurally, it is characterized as being loosely packed thin fibrils with fairly uniform diameters. It is produced by smooth muscle fibroblasts, reticular cells, Schwann cells, and hepatocytes.

Collagen type IV is found in the epithelial and endothelial basal lamina and basement membranes. The primary function of type IV collagen involves support and filtration. Microscopically, it appears as a thin, amorphous, weakly birefringent membrane. Ultrastructurally, it appears to have neither fibers nor fibrils.

Collagen type V is found in fetal membranes, blood vessels, placental basement membrane, and in small amounts in other tissues. This type of collagen remains largely uncharacterized.

B. Structure Of Collagen

The principal amino acids found in collagen are glycine, proline and hydroxyproline. Hydroxylysine is also characteristic of collagen. These hydroxy amino acids are the result of hydroxylation of proline and lysine present in nascent collagen polypeptides during collagen synthesis. The collagen content in a tissue can be determined by measurement of its hydroxyproline content.

Collagen is comprised of polypeptide chains, designated as "$\alpha$." There are two types of $\alpha$ chains, referred to as "alpha-1" ("$\alpha$ 1") and "alpha-2" ("$\alpha$-2"). The most important types of $\alpha$ 1 chains are $\alpha 1(I)$, $\alpha 1(II)$, $\alpha 1(III)$, and $\alpha 1(IV)$, which aggregate in different combinations to produce the triple helices of types I, II, III, IV, and V. Type I collagen is composed of two $\alpha 1$ and one $\alpha 2$ chains. It's formula is $(\alpha 1[I])_2 \alpha 2$. The formula for type II collagen is $(\alpha 1[II])_3$, while the formula for type III collagen is $(\alpha 1[III])_3$, and type IV is $(\alpha 1[IV])_3$.

"Tropocollagen" is the protein unit that polymerizes into aggregations of microfibrillar subunits packed together to form "collagen fibrils." Hydrogen bonds and hydrophobic interactions are critical in this aggregation and packing. Covalent crosslinks reinforce the structure of the collagen fibrils. Collagen fibrils are thin and elongated, of variable diameter, and have transverse striations with a characteristic periodicity of 64 nm. The transverse striations is produced by the overlapping organization of the subunit tropocollagen molecules. In type I and III collagen, these fibrils associate to produce collagen "fibers." In collagen type I, collagen "bundles" may be formed by association of the fibers. Collagen type II is observed as fibrils, but does not form fibers, while types IV and V do not form fibrils or fibers.

Collagen fibers are the most abundant fiber found in connective tissue. Their inelasticity and molecular configuration provide collagen fibers with a tensile strength that is greater than steel. Thus, collagen provides a combination of flexibility and strength to the tissues in which it resides. In many parts of the body, collagen fibers are organized in parallel arrays to form collagen "bundles."

When fresh, collagen fibers appear as colorless strands, although when a large number of fibers are present, they cause the tissues in which they reside to be white (e.g., tendons and aponeuroses). The organization of the elongated tropocollagen in the fibers cause them to be birefringent. Staining with certain acidic dyes (e.g., Sirius red) enhances this birefringency. As this increase in birefringency us only observed in oriented collagen structures, it is useful as a method to detect the presence of collagen in a tissue.

C. Properties and Uses of Collagen

There are many properties of collagen that make it an attractive substance for various medical applications, such as implants, transplants, organ replacement, tissue equivalents, vitreous replacements, plastic and cosmetic surgery, surgical suture, surgical dressings for wounds, burns, etc. (See e.g., U.S. Pat. Nos. 5,106,949, 5,104,660, 5,081,106, 5,383,930, 4,485,095, 4,485,097, 4,539,716, 4,546,500, 4,409,332, 4,604,346, 4,835,102, 4,837,379, 3,800,792, 3,491,760, 3,113,568, 3,471,598, 2,202,566, and 3,157,524, all of which are incorporated herein by reference; J. F. Prudden, Arch. Surg. 89:1046–1059 [1964]; and E. E. Peacock et al. Ann. Surg., 161:238–247 [1965]). For example, by itself, collagen is a relatively weak immunogen, at least partially due to masking of potential antigenic determinants within the collagen structure. Also, it is resistant to proteolysis due to its helical structure. In addition, it is a natural substance for cell adhesion and the major tensile load-bearing component of the musculoskeletal system.

Thus, extensive efforts have been devoted to the production of collagen fibers and membranes suitable for use in medical, as well as veterinary applications.

Collagen has been used in the area of soft tissue augmentation, as a replacement for paraffin, petrolatum, vegetable oils, lanolin, bees wax, and silicone previously used. (See e.g., U.S. Pat. No. 5,002,071, herein incorporated by reference). However, problems have been associated with the use of collagen in implants. As the non-collagenous proteins present in impure collagen preparations are more potent immunogens than the collagen, and can stimulate the inflammatory response, it is critical that highly pure collagen be used. If the inflammatory cascade is stimulated, the resorption of collagen occurs by the infiltrating inflammatory cells (e.g., macrophages, and granulocytes) that contain collagenase, resulting in thee digestion of the collagen. In addition, collagen itself is chemotactic, and becomes increasingly chemotactic as it is degraded into smaller peptide fragments. Also, there are concerns associated with the use of non-human collagen. For example, a repeatedly documented problem associated with the use of bovine collagen as a biomaterial is the consistent, chronic cellular inflammatory reaction that is evident following its implantation or use. This inflammation may result in residual scar tissue formation, adhesion formation, interference with healing of skin edges, pseudointima formation, pseudodiaphragm formation, disruption of anastomoses, transient low grade fever, aneurysms, or other problems.

D. Preparation Of Collagen

Collagen preparations are typically prepared from skin, tendons (e.g., bovine Achilles, tail, and extensor tendons), hide or other animal parts, by procedures involving acid and/or enzyme extraction. Basically, collagen preparation methods involve purification of collagen by extraction with diluted organic acids, precipitation with salts, optional gelation and/or lyophilization, tangential filtration etc. After separating facia, fat and the impurities, the tissue is subjected to moderate digestion with proteolytic enzymes, such as pepsin, then the collagen is precipitated at a neutral pH, redissolved and the residual impurities precipitated at an acid pH. The tissue is then digested with a strong alkali and then exposed to acid to facilitated swelling. The collagen fibers are then precipitated with salts or organic solvents, and dehydrating the collagen fibers. (See e.g., U.S. Pat. No. 5,028,695, herein incorporated by reference). Eventually the extracted collagen can be converted into a finely divided fibrous collagen by treating water-wet collagen with acetone to remove water, centrifuging to obtain the solid mass of collagen and deaggregating the collagen during drying. (See e.g., U.S. Pat. No. 4,148,664, herein incorporated by reference). The collagen preparation can then be brought back to a neutral pH and dried in the form of fibers. Completely transparent, physiological and hemocompatible gels, collagen films, and solutions can be prepared. These forms of collagen may then be used in the fabrication of contact lenses and implants.

One disadvantage of treatment with pepsin, is that the collagen preparation may be partially degraded (i.e., the extraction enzymes cleave the collagen molecule at the terminal non-helical regions, which contain the intercollagenous cross-linkages). Indeed, it has been found that collagen extracted with pepsin results in preparations that are too weak for certain applications, especially those for which substantial mechanical handling of the collagen preparation is required.

Some acid treatments also have disadvantages. For example, the acid process described by Chvapil (M. Chvapil et al., Intl. Rev. Connective Tiss. Res., 6:1–55 [1979]) involves acid solubilization of bovine tendon collagen to produce a collagen suspension. This suspension is then either dialyzed or precipitated in saline, resulting in an amorphous precipitate containing non-fibrillary denatured collagen. Collagen prepared according to this method is generally not directly suitable for medical purposes, as it lacks tensile strength in moist media and has little resistance against enzymatic degradation when applied to living tissue. In addition, denatured collagen or collagen that has undergone treatment to reform the physical and biological characteristics to approximate collagen in vivo is often not satisfactory. It often lacks the mechanical properties required for wet dressings, as it lacks the in vivo organized structure (i.e.,collagen fibers are not present in this artificial collagen).

Thus, current methods for collagen preparation are unsatisfactory. Clearly, there is a need for the development of improved methods for the high volume production of high quality collagen suitable for use in medical treatment.

SUMMARY OF THE INVENTION

The present invention relates to methods for preparing collagen from humans and other animals. In particular, the present invention provides methods for the preparation of collagen suitable for biomedical applications.

The present invention provides numerous embodiments for the purification of collagen. It is particularly preferred that the collagen purified according to one embodiment of the present invention be type I collagen.

In one embodiment, the present invention provides a method for purifying collagen comprising: providing a sample comprising collagen, first and second proteolytic enzyme preparations, and a reducing agent; exposing the collagen sample to the first proteolytic enzyme preparation to produce a first collagen solution; exposing the first collagen solution to the reducing agent to produce a second collagen solution; exposing the second collagen solution to the second proteolytic enzyme preparation to produce purified collagen.

In one alternative embodiment, the method of the present invention further comprises the step of de-epithelializing the sample prior to exposing the sample to the first proteolytic enzyme preparation.

In a preferred embodiment, the first and/or second proteolytic enzyme preparation comprises an enzyme in the cysteine class. In a particularly preferred embodiment, the first and/or second proteolytic enzyme preparation comprises papain.

In an alternate embodiment of the method of the present invention, the reducing agent is selected from the group consisting of sodium sulfide, dithiothreitol, glutathionine, and sodium borohydride. In a preferred embodiment, the reducing agent comprises sodium borohydride.

In yet another embodiment, the method of the present invention comprises the further step of exposing the purified collagen to a delipidation agent to produce dilipidated collagen. In a preferred embodiment of this method, the delipidation agent comprises a mixture comprising chloroform and methanol.

In a particularly preferred embodiment, the method of the present invention further comprises the steps of compressing the delipidated collagen to produce compressed collagen; dehydrating the compressed collagen to produce dehydrated collagen; and dispersing and drying the dehydrating collagen to form collagen fibers. Thus, in this embodiment of the methods of the present invention, the collagen fibers are dried.

In another alternative embodiment, the method of the present invention comprises the step of exposing the delipidated collagen to a phosphorylating agent to produce phosphorylated collagen. In a preferred embodiment, the phosphorylation agent is selected from the group consisting of sodium trimetaphosphate, sodium hexametaphosphate, sodium ultraphosphate, sodium tetrametaphosphate, phosphoric anhydride, and phosphoryl trichloride. In a particularly preferred embodiment, the phosphorylation agent comprises sodium trimetaphosphate. In an alternatively preferred embodiment, the purified collagen comprises CollagenPRO™.

In one embodiment, the present invention provides purified collagen purified by the steps of: providing a sample comprising collagen, first and second proteolytic enzyme preparations, and a reducing agent; exposing the collagen sample to the first proteolytic enzyme preparation to produce a first collagen solution; exposing the first collagen solution to the reducing agent to produce a second collagen solution; exposing the second collagen solution to the second proteolytic enzyme preparation to produce purified collagen.

It is further contemplated that the purified collagen be comprised of additional compounds, including but not limited to antimicrobials, antivirals, growth factors, antidehydration compounds, antiseptics, or other compounds suitable for biomedical and/or veterinary uses.

The present invention also provides an alternative embodiment comprising methods for production of biocompatible collagen, in which the method comprises: providing a sample comprising collagen, first and second proteolytic enzyme preparations, a reducing agent, a delipidation agent, and a phosphorylation agent; exposing the collagen sample to the first proteolytic enzyme preparation to produce a first collagen solution; exposing the first collagen solution to the reducing agent to produce a second collagen solution; exposing the second collagen solution to the second proteolytic enzyme preparation to produce to produce a proteolyzed collagen solution; exposing the proteolyzed collagen solution to the delipidation agent to produce delipidated collagen; and exposing the delipidated collagen to the phosphorylation agent to produce phosphorylated collagen.

In an alternative embodiment, the method of the present invention further comprises the step of de-epithelializing the sample prior to exposing the sample to the first proteolytic enzyme preparation.

In a preferred embodiment, the first and/or second proteolytic enzyme preparation of the method comprises an enzyme in the cysteine class. In a particularly preferred embodiment, the first and/or second proteolytic enzyme preparation comprises papain.

In an alternate embodiment of the method of the present invention, the reducing agent is selected from the group consisting of sodium sulfide, dithiothreitol, glutathionine, and sodium borohydride. In a preferred embodiment, the reducing agent comprises sodium borohydride.

In an alternative embodiment, the delipidation agent comprises a mixture of chloroform and methanol. In yet another embodiment, the phosphorylation agent is selected from the group consisting of sodium trimetaphosphate, sodium hexametaphosphate, sodium ultraphosphate, sodium tetrametaphosphate, phosphoric anhydride, and phosphoryl trichloride. In a particularly preferred embodiment, the phosphorylation agent comprises sodium trimetaphosphate.

In yet a further embodiment, the method of the present invention further comprises the steps of compressing the delipidated collagen to produce compressed collagen; dehydrating the compressed collagen to produce dehydrated collagen; and dispersing and drying the dehydrating collagen to form collagen fibers. Thus, in this embodiment of the methods of the present invention, the collagen fibers are dried.

In a particularly preferred embodiment, the method further comprises the step of filter-sterilizing the delipidated collagen prior to exposing the delipidated collagen to the phosphorylation agent to produce phosphorylated collagen.

The present invention also provides purified such that the collagen is biocompatible. In this embodiment, the biocompatible collagen is produced by the method of: providing a sample comprising collagen, first and second proteolytic enzyme preparations, a reducing agent, a delipidation agent, and a phosphorylation agent; exposing the collagen sample to the first proteolytic enzyme preparation to produce a first collagen solution; exposing the first collagen solution to the reducing agent to produce a second collagen solution; exposing the second collagen solution to the second proteolytic enzyme preparation to produce to produce a proteolyzed collagen solution; exposing the proteolyzed collagen solution to the delipidation agent to produce delipidated collagen; and exposing the delipidated collagen to the phosphorylation agent to produce phosphorylated collagen. In one preferred embodiment, the phosphorylated collagen comprises CollagenPRO™.

In another preferred embodiment, the biocompatible collagen comprises a film or membrane, while in alternate preferred embodiments, the biocompatible collagen comprises a solid, while in other alternately preferred embodiments, the biocompatible collagen comprises a solution. In other embodiments, the biocompatible collagen is a dried film that is hydrated prior to its application.

It is further contemplated that the biocompatible collagen be comprised of additional compounds, including but not limited to antimicrobials, antivirals, growth factors, antidehydration compounds, antiseptics, or other compounds suitable for biomedical and/or veterinary uses.

The present invention also provides methods for achieving hemostasis comprising: providing purified and/or biocompatible collagen purified as described above, and a bleeding wound; and exposing the purified and/or biocompatible collagen to the bleeding wound.

The present invention also provides a method of transplantation comprising providing: purified and/or biocompatible collagen, and a transplantation site; and exposing the purified and/or biocompatible collagen to the transplantation site.

DESCRIPTION OF THE INVENTION

Figure 1:
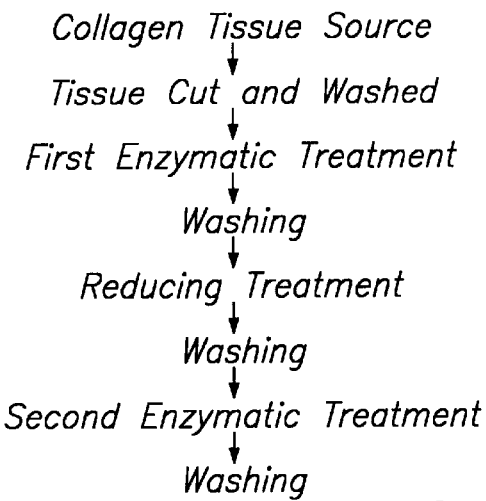
FIG. 1 is a flow chart of one embodiment of the Twice Treatment Process™ (TTP™).

The present invention relates to methods for preparing collagen from tissues of humans and other animals. In particular, the present invention provides methods for the preparation of collagen suitable for biomedical, veterinary, and other applications.

The present invention was developed in order to address the problems presented by commonly used collagen preparations. The present invention is predicated in part on the discovery that collagen may be prepared in a manner in which all non-collagenous materials are removed, while retaining the native molecular quaternary structure and other characteristic features of collagen (e.g., length, diameter, and periodicity of collagen type I fibrils, as described above). The methods of the present invention facilitate the enzymatic removal of all extraneous materials while preserving the native collagen molecules in their original fiber configuration. The processes of the present invention may be used to prepare highly purified collagen from various animal sources (including humans), as most if not all, conjugated proteolipids and phospholipid contaminating the source collagen are removed through use of a specific mixture of organic solvents. In various embodiments, the prepared collagen of the present invention has better wound healing and hemostatic properties than collagen preparations previously developed.

Unlike previously reported enzymatic methods in which papain is used (e.g, U.S. Pat. No. 3,529,530 and 5,316,942, herein incorporated by reference) for collagen preparation, the methods of the present invention utilize a two-step enzyme treatment process. In one embodiment, the two-step treatment process ("Twice Treatment Process™" or "TTP™") of the present invention renders collagen polymers non-inflammatory through the processes in which papain or other proteolytic enzymes are used in conjunction with oxidative and reducing agents. The "twice-treatment" refers to the use of proteolytic enzyme in two steps: a first proteolytic treatment is conducted, followed by treatment with a reducing agent, which is then followed by a second proteolytic treatment. In particularly preferred embodiments, this process is followed by removal of proteolipids and phospholipids using a solution of chloroform and methanol. In additional embodiments, the collagen is bioactivated by varied degrees of controlled phosphorylation.

The use of papain was contemplated as providing a safe means for treating collagen intended for human use, as it is traditionally used in the food industry and in association with wound cleansers. In comparison with pepsin, the enzyme most commonly used to prepare collagen for biomedical applications, better results in terms of reduced immunogenicity was obtained with papain. Papain, an enzyme extracted from papaya, is known to break the disulfide bonds of cysteine. As many immunogenic molecules contain cystine disulfide bonds, papain may be used to degrade these molecules and render them non-immunogenic. For example, papain is capable of digesting numerous naturally occurring proteins and peptides, as well as benzoyl amino acid esters (See e.g., Smith and Kimmel, *Enzymes, The*, vol. 4, 2d ed., Academic Press, NY, page 138 [1960]). In addition, papain has been reported to have a lytic effect of elastin, one of the contaminants that is difficult to remove from purified collagen (See e.g., Coulson, Biochim. Biophys. Acta 237:378 [1971]; and Smith et aL, Nature 198:1311 [1963]).

Initial experiments involving a one-step papain treatment to remove immunogenic sites from collagen were largely unsuccessful in altering the in vivo performance of purified collagen (See, Example 3, below). These observations led to the development of the methods of the present invention, which result in the breaking and loosening of the natural crosslinks of collagen fibers (e.g., aldol condensation). In this manner, the papain used in the second treatment (i.e., papain is used in two treatment steps) is provided access to most, if not all of the collagen molecules' surfaces, and facilitates the release of trapped immunogenic sites from the collagen preparation. These developments resulted in one embodiment of the present invention, in which papain is used at two specific stages of the process (i.e., before and after the treatment the collagen with a reducing and/or a unfolding agent). These methods therefore, provide means to produce highly purified collagen that is non-immunogenic.

In a preferred embodiment, a delipidation process is contemplated, in which solvents are used to remove proteolipids and phospholipids. Early attempts to remove these compounds from collagen using single organic solvent(s) such as ether, acetone, ethanol, isopropyl alcohol, etc. were not effective in removing all the proteolipids or conjugated lipids like proteolipids. (See, Example 4). Therefore, a unique technique was developed in which a 3:1 v/v mixture of chloroform : methanol was used to remove all the proteolipids and phospholipids.

In a preferred embodiment, purified collagen may be chemically-modified by covalently binding phosphates to hydroxyl groups of hydroxylated amino acids, as shown in Example 6. Although it is not necessary to understand the present invention, this reaction likely involves covalent bonding of phosphate to hydroxyl group of serine, tyrosine and/or threonine, hydroxylysine and hydroxyproline. The reaction is controlled, in order to limit the degree of reaction. At the completion of this step, any of the potentially remaining reactive groups present in the collagen may be fully converted to phosphoryl, hydroxyl, or sulfonyl groups by exposure to trimetaphosphate or other active agents. The end product with different degrees of chemical modification or without the same that is either soluble or insoluble in a physiological buffer and is suitable for numerous applications. In this manner, the purified product can be customized to particular uses. For example, bioactive responses may be favored by reacting the collagen with a linear or cyclic polyphosphates at alkaline pH.

The final collagen product may be used in solution or as a solid, and has been shown to be useful for a variety of purposes, including but not limited to, biological implants, grafts, transplants, and drug delivery. It is, moreover, contemplated that it is useful as a surgical adjunct during transplant surgery and to prevent post-operative graft dislocation, as a hemostatic agent, to augment soft tissues, and as a support for in vitro cell growth (i.e., in cell cultures).

When used as a hemostatic agent, the collagen prepared according to the methods of the present invention is particularly applicable to the control of bleeding from surfaces, especially large surfaces. For example, the collagen of the present invention may be used as a hemostatic agent on cut or severed bone, organs (e.g., spleen, liver or kidney which has been cut surgically or traumatically), the central nervous system with its predominant collection of small blood vessels, prosthetic surgery, oozing surfaces resulting from the surgical removal of necrotic tissue, cosmetic surgery, and any surfaces with oozing of blood from one or more small sources (e.g. facial cuts). This hemostatic collagen preparation may be applied in a variety of forms (e.g., as a powder applied directly to the surface; as a styptic in pencil form; as a gel, a sponge or in fabric form). The amount of hemostatic collagen preparation utilized will vary with the extent of the bleeding, the surface area to be treated, and severity of the blood flow; the only requirement being that the achievement of the desired control.

Definitions

To facilitate understanding of the invention, a number of terms are defined below.

The terms "specimen" or "sample" are used interchangeably in the present specification and claims and are used in their broadest sense. On the one hand they are meant to include a clinical specimen (i.e., sample) or culture (e.g., microbiological cultures). On the other hand, it is meant to include both biological and environmental samples. Biological samples may be animal, including human, fluid or tissue, food products and ingredients. However, these examples are not to be construed as limiting the sample types applicable to the present invention.

The "non-human animals" of the invention comprise any animal other than humans. Such non-human animals include vertebrates such as rodents, non-human primates, ovines, bovines, ruminants, lagomorphs, porcines, caprines, equines, canines, felines, aves, etc. Although it is not intended that the present invention be limited to any particular animal, preferred non-human animals are selected from livestock, such as bovines and ovines.

As used herein, the term "procollagen" is used in reference to the precursor protein that is cleaved in the extracellular matrix to form collagen. In particular, procollagen is used in reference to "pro-α chains" that are precursors of the collagen α chains. Pro-α chains are characterized as comprising "pro-peptides" that are important in the formation of the triple-helix formation of procollagen.

As used herein, the term "collagen" is used in reference to the extracellular family of fibrous proteins that are characterized by their stiff, triple-stranded helical structure. Three collagen polypeptide chains ("α-chains") are wound around each other to form this helical molecule. The term is also intended to encompass the various types of collagen, although the preferred form is type I collagen.

As used herein, the term "collagen sample" refers to any source of collagen, including, but not limited to hide, skin, tendons, blood vessels, intestine, liver, spleen, heart valve, bone, etc. It is not intended that the source of collagen sample be limited to any particular tissue source or type. The only requirement is that the collagen sample contain the type of collagen of interest to be purified (e.g., type I collagen). However, it is not intended that the present invention be limited to any particular type of purified collagen.

As used herein, the term "collagen fibrils" is used in reference to the long, thin polymers of collagen that are grouped into bundles referred to as "collagen fibers." The "collagen matrix" refers to an extracellular matrix of collagen, with the characteristic periodic cross-striations that may be visible through electron microscopy. Characteristically, the collagen matrix is formed when normal collagen molecules are assembled in a quarter stagger array in a three-dimensional structure appearing by electron microscopy as a 67 nanometer striation.

As used herein, the term "compressed collagen" refers to a collagen sample that has been compressed due to the application of pressure. In preferred embodiments, the collagen to be compressed is wet, TTP™-treated, and delipidated collagen. It is intended that this compression be accomplished by any means (i.e., hand presses or machine presses). It is intended that this compression encompass a range of pressures, ranging from 5,000 to 50,000 pounds per square inch (psi) of sample. In preferred embodiments, the pressure applied is approximately 9,000, while in alternative preferred embodiments, the applied pressure is approximately 30,000. In particularly preferred embodiments, the compressed collagen is in the form of a cake.

As used herein, the term "dehydrated collagen" refers to a collagen sample that has been dehydrated using any method commonly known in the art. In preferred embodiments, dehydrated collagen is produced by lyophilization or desiccation.

As used herein, the term "drying" refers to any method for the removal of water from a sample. It is intended that the term encompass methods including, but not limited to, air-drying and heating.

As used herein, the term "dispersing" refers to the mechanical separation of a sample. For example, it is intended that the term encompass the separation of the components contained within a cake of compressed collagen. In this embodiment, the components of the compressed cake are dispersed into fibers. In preferred embodiments, the collagen is agitated and suspended within a liquid. These fibers comprise collagen fibers as described above (i.e., bundles of collagen fibrils). Thus, it is intended that native, as well as dried collagen fibers be encompassed by this definition.

As used herein, the term "hemostatic" refers to an agent that stops or slows the flow of blood.

As used herein, the term "proteolytic agent" refers to any enzyme (alone or in a mixture of enzymes) that is capable of hydrolyzing or cleaving proteins. It is intended that the term encompass any enzyme with proteolytic properties, including, but not limited to the cysteine class of enzymes which reacts with cysteine moieties in their substrates. This class of enzymes includes, but is not limited to glyceraldehydephosphate dehydrogenase, and papain.

In particular, it is contemplated that the term refer to enzymes that are capable of degrading proteins associated with collagen, while leaving collagen type I in its native configuration. However, it is contemplated that in some embodiments, the proteolytic agent breaks the cross-links associated with collagen fibers in collagen. In this manner, the cross-links between the strands within the fibers are loosened, such that the fibers retain their basic shape, but sufficient space is allowed between the fibers that molecules that are normally trapped within the collagen fiber structure may be removed.

As used herein, the term "proteolyzed collagen" refers to collagen that has been treated with at least one proteolytic enzyme.

As used herein, the term "purified" refers to the removal of contaminants from a sample. For example, it is intended to encompass proteolyzed collagen. It is not intended that the term be limited to any particular level of purity. However, in preferred embodiments, the purified sample is treated with proteolytic enzymes, In particularly preferred embodiments, the purified sample has undergone subsequent treatments, including but not limited to, delipidation and/or phosphorylation.

As used herein, the term "reducing agent" refers to any compound or mixture of compounds that is capable of reducing another compound. In this process the proportion of hydrogen is increased while the proportion of oxygen is decreased and the number of multiple bonds is decreased. In particular, it is intended that the term encompass any agent that is capable of unfolding proteins from their native configurations by breaking disulfide bonds. Such agents include, but are not limited to compounds such as sodium sulfide, dithiothreitol, glutathionine, and sodium borohydride. The term "reduced collagen" refers to collagen that has been exposed to or treated with at least one reducing agent.

As used herein, the term "phosphorylation agent" refers to any compound or mixture of compounds that is capable of phosphorylating another compound. Such compounds include, but are not limited to sodium trimetaphosphate, sodium hexametaphosphate, sodium ultraphosphate, sodium tetrametaphosphate, phosphoric anhydride, and phosphoryl trichloride.

As used herein, "phosphorylated collagen" refers to collagen that has been treated so as to increase the number of phosphorylated amino acids in the collagen molecules. It is intended that the term encompass a range of phosphorylation, from a minimal degree of phosphorylation (i.e., only one amino acid has been phosphorylated) to a maximal degree of phosphorylation (i.e., all of the amino acids available and suitable for phosphorylation have been phosphorylated), or any degree of phosphorylation within this range.

As used herein, the term "delipidation agent" refers to any compound or mixture of compounds that is capable of removing lipid moieties (i.e., delipidating). In particular it is intended that the term encompass substances that are capable of removing molecules including, but not limited to, phospholipids, neutral lipids, proteolipids, and glycolipids from collagen. Such substances include organic solvents such as chloroform and methanol. The term "delipidated collagen" refers to collagen that has been exposed to or treated with at least one delipidation agent. In particularly preferred embodiments, the delipidation agent is chloroform and methanol in a 3:1 mixture.

As used herein, "alkali" refers to a hydroxide of one of the alkali metals (e.g., lithium, sodium, potassium, rubidium, cesium, and francium). It also encompasses substances which provide an alkaline solution (pH>7) in water (e.g., CaO, Ca(OH)$_2$, and Na$_2$CO$_3$.

As used herein, "modified collagen" refers to collagen that has been chemically modified by such means as phosphorylation, fluorination, halogenation (e.g., chlorination), sulfonation, and/or hydroxylation.

As used herein, the term "filter-sterilized" sample refers to a sample that has been applied to a filter to remove unwanted contaminants such as bacteria, from the sample.

As used herein, "de-epithelialization" refers to the process of removing epithelial tissues and/or cells from a sample. The term "epithelial" pertains to epithelium, the cellular covering of internal and external body surfaces.

As used herein, "biocompatible collagen" refers to collagen that is suitable for biomedical or veterinary applications, including but not limited to grafts, and implants.

As used herein, "biomolecule" refers to any molecule that has biomedical or veterinary applications. For example, it is intended to encompass various compounds and substances, including collagen, synthetic polymers, or other materials useful for implantation, transplantation, and/or grafting.

The term "graft" refers to any tissue or organ for implantation or transplantation, as well as the process of implantation or transplantation of such tissue. For example, a skin graft is a piece of skin or other tissue or material that is transplanted in order to replace a lost porton of the skin. It is intended that the term encompass materials such as purified collagen or other suitable biocompatible substances useful in the replacement of lost or damaged tissues or organs. In particular, the term "graft" is used in reference to the replacement of skin or other tissues or organs exposed to the environment. For example, the term may be used in reference to such tissues as skin, cutaneous tissues, mucous membranes, conjunctival membranes, etc. However, it is not intended that the term be limited to any particular type of tissue.

The term "transplant" refers to tissue used in grafting, implanting, or transplanting, as well as the transfer of tissues from one part of the body to another, or the transfer of tissues from one individual to another, or the introduction of biocompatible materials into or onto the body. The term "transplantation" refers to the grafting of tissues from one part of the body to another part, or to another individual. However, it is also intended that the tissue or organ used for transplantation or grafting be comprised of materials such as collagen purified according to the methods of the present invention. Thus, it is not intended that the graft or transplant be limited to naturally-occurring tissues.

As used herein, the term "implantation" refers to the insertion of an organ or tissue in a new site in the body, as well as the insertion of any biocompatible, biological, living, inert, or radioactive material into the body. The term "implant" refers to the process of inserting or grafting of tissue, inert, living, radioactive, or biocompatible material into intact tissues or a body cavity, as well as the material to be so inserted or grafted.

As used herein, the term "flap" refers to a mass of tissue for grafting, which usually includes skin, that is only partially removed from one part of the body, so that it retains its own blood supply during transfer to another site of the body or to another individual. It is also intended that the term encompass masses of tissue for grafting or implantation that have been cultivated in vitro prior to their grafting or implantation.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); Å (angstrom); xg or x g (times gravity); w/w (weight to weight); w/v (weight to volume);° C. (degrees Centigrade); rpm (rotations per minute); normal saline (0.9% NaCl solution, pH 6.2±0.3); Harlan Sprague Dawley (Harlan Sprague Dawley, Inc., Madison, Wis.); Fisher (Fisher Scientific, Pittsburgh, Pa.); Sigma (Sigma Chemical Co., St. Louis, Mo.); Aldrich (Aldrich Chemical Company, Inc., Milwaukee, Wis.); Spectrum (Spectrum Chemicals, Inc., Gardena, Calif.); American (American Dade, Division of American Hospital Supply Co., Dade, Fla.); PDL (Protein Design Laboratories, Mountain View, Calif.); Nitabell Rabittry (Nitabell Rabittry, Hayward, Calif.); Axygen (Axygen, Inc., Hayward, Calif.): Arizona Health Sciences (Arizona Health Sciences Center, Tucson, Ariz.); Collaborative Research (Collaborative Research, Inc., Bedford, Mass.); Medchem Products (Medchem Products, Woburn, Mass.); Collatek (Collatek, Inc., Plainsboro, N.J.); Boehringer Mannheim (Boehringer Mannheim, Indianapolis, Ind.); J & J Medical (J & J Medical, Inc., Arlington, Tex.); Axygen (Axygen Inc., Hayward, Calif.); Papain Products (Papain Products, Tamilnadu, India); Beckman (Beckman Instruments, Inc., Fullerton, Calif.); and Brinkmann (Brinkmann Instruments, Inc., Westbury, N.Y.).

Unless otherwise indicated, all chemicals were obtained from commercial suppliers such as Sigma, Fisher, or Spectrum. All of the solvents used in these Examples were obtained from Spectrum Chemicals, and were spectrophotometric or reagent grade. The papain used in these Examples was obtained from Sigma or Papain Products.

EXAMPLE 1

Isolation and Purification of Collagen With Papain

In this Example, collagen was purified from dehaired bovine hide, using a one-step enzyme treatment process.

First, 100 g of clean, dehaired bovine hide obtained from a local slaughterhouse was chopped or sliced into pieces of approximately 1 cm thickness and approximately 10 cm long. The cut slices were washed in three liters of a wash buffer containing double distilled water containing 30 g NaCl, 3 g ZnCl, 4.5 g methyl paraben, 0.9 g propyl paraben. In some experiments, the wash buffer contained 30.0 g NaCl, 3 g ZnCl, 4.5 g methyl paraben, and 1.5 g trichlorophenate or 3 g hypochlorite. No differences were observed in the purified collagen preparations using these different wash buffers. Washing was conducted at 5°–15° C. for 6–8 hours under constant agitation using a Rotator (Model #4140, American). The wash procedure was repeated twice, with the fluid being decanted from the solids after each wash. The repeated wash procedure removed most of the albumins and globulins that usually constitute approximately 1–5% of the dry weight of the sample.

Prior to application of the enzyme treatment, de-epithelialization of the sample was conducted. In this process, 1 liter of cold de-epithelialization buffer containing cold deionized water containing 24 g NaOH and 56 g calcium oxide was added to the previously washed sample, and centrifuged at 5,000×g for 15 minutes to obtain solid chunks of material. The sample was agitated on a rotator at 80–100 rpm, for 48 hours at 15° C. The de-epithelialization solution was replaced every 16 hours. At the end of 48 hours, the chunks were soaked in 3 liters of deionized water for 2 hours, with agitation at 80–100 rpm, and the solids were recovered by centrifugation at 5,000×g for 15 min. One hundred grams of boric acid solubilized in 3 liters of deionized water pre-chilled to 4° C., was added and the sample was agitated for 16 hours at 4° C. The pH was measured and adjusted to approximately 8.3. The sample was washed twice with 3 liters of deionized water for 2 hours each wash, and the solids were recovered by centrifugation as described above. Although this method was used in this Example, various methods for achieving de-epithelization of samples are available, and known to those in the art. It is contemplated that any of these standard methods available to those in the are will be successful in achieving the desired de-epithelization.

After washing, the sample was treated with papain in a one-step enzymatic treatment. In this process, the sample was further washed in 3 liters of pyrogen-free deionized water for 2 hours at room temperature. The sample was centrifuged for 15 minutes at 5,000×g, and decanted. One liter of normal saline solution was then added to the sample. Papain (Sigma or Papain Products) was added at the rate of 1–2 mg per ml of the total volume (i.e., 1 liter), with continual stirring. Following addition of the papain, the solution was incubated under agitation using a rotator at 80–100 rpm, at 37° C. for approximately 16 hours.

Following this first enzyme treatment, the excess water was drained and the solids were washed three times with 2 liters of deionized water. One liter of 0.2M sodium borohydride was then added to the washed solids. The solids were incubated for 3 hours under agitation with a rotator at 80–100 rpm. The excess water was drained, and the solids were washed three times with 2 liters of deionized water.

Robust Treatment

In addition to the normal enzyme treatment followed by reducing treatment, as described above, a "Robust Treatment" was also tested. In this treatment, a multifold increase in time of incubation and enzyme concentration were used, as compared to the "normal" treatment. Although the rest of the steps were the same as described for the normal treatment (i.e., the collagen used in the "Robust Treatment" was prepared using the same bovine hide, cutting and washing steps), in the Robust Treatment, 4 mg of papain was added per ml of solution and 24 hours of incubation were used in the enzymatic treatment step, rather than the 1 mg of papain per ml of solution and 16 hours of incubation.

The amount of remaining contaminants and collagen in this preparation was determined and compared with the results obtained using the methods described in Example 2.

EXAMPLE 2

Isolation and Purification of Type I Collagen

This Example describes the methods and aspects of the development of the "Twice-Treatment Process™" (TTP™) of one embodiment of the present invention.

In this Example, the "Twice-Treatment Process™" (TTP™) is described. In this Example, type I collagen was purified from dehaired bovine hide. First, 100 g of clean, dehaired bovine hide obtained from a local slaughterhouse was chopped or sliced into pieces of approximately 1 cm thickness and approximately 10 cm long. The cut slices were washed in three liters of a wash buffer containing double distilled water containing 30 g NaCl, 3 g ZnCl, 4.5 g methyl paraben, 0.9 g propyl paraben. In some experiments, the wash buffer contained 30.0 g NaCl, 3 g ZnCl, 4.5 g methyl paraben, and 1.5 g trichlorophenate or 3 g hypochlorite. No differences were observed in the purified collagen preparations using these different wash buffers. Washing was conducted at 5°–15° C. for 6–8 hours under constant agitation using a rotator (Model #4140, American) at 80–100 rpm. The wash procedure was repeated twice, with centrifugation at 5,000×g for 15 minutes, and decanting of the supernatant each time. The repeated wash procedure removed most of the albumins and globulins that usually constitute approximately 1–5% of the dry weight of the sample.

Prior to application of the enzyme treatment, de-epithelialization of the sample was conducted. In this process, 1 liter of cold de-epithelialization buffer containing cold deionized water containing 24 g NaOH and 56 g calcium oxide was added to the previously washed sample, and centrifuged at 5,000×g for 15 minutes to obtain solid chunks of material. The sample was agitated on a rotator at 80–100 rpm, for 48 hours at 15° C. The de-epithelialization solution was replaced every 16 hours. At the end of 48 hours, the chunks were soaked in 3 liters of deionized water for 2 hours, with agitation at 80–100 rpm, and the solids were recovered by centrifugation at 5,000×g for 15 min. One hundred grams of boric acid solubilized in 3 liters of deionized water pre-chilled to 4° C., was added and the sample was agitated for 16 hours at 4° C. The pH was measured and adjusted to approximately 8.3. The sample was washed twice with 3 liters of deionized water for 2 hours each wash, and the solids were recovered by centrifugation as described above. Although this method was used in this Example, various methods for achieving de-epithelization of samples are available, and known to those in the art. It is contemplated that any of these standard methods available to those in the are will be successful in achieving the desired de-epithelization.

After washing, the sample was treated with the TTP™. In this process, the sample was further washed in 3 liters of pyrogen-free deionized water for 2 hours at room temperature, and the water was decanted. One liter of normal saline solution was then added to the sample. Papain was added at the rate of 1–2 mg per ml of the total volume (i.e., 1 liter), with continual stirring. Following addition of the papain, the solution was incubated under agitation on a rotator at 80–100 rpm, at 37° C. for approximately 16 hours.

Following this first enzyme treatment, the excess water was drained and the solids were washed three times with 2 liters of deionized water. One liter of 0.2M sodium borohydride was then added to the washed solids. The solids were incubated for 3 hours under agitation with a rotator at 80–100 rpm. The excess water was drained, and the solids were washed three times with 2 liters of deionized water. The second enzyme treatment was then conducted on the solids, using the same procedure described above for the first enzyme treatment. A strong reducing agent was found to be essential. Although it is not essential to understanding or using the present invention, it may be that this strong reducing agent stabilizes any reversibly reactive group that might remain following the first enzyme treatment. This step also reduced the amount of aldehyde potentially involved in aldol condensation reactions (i.e., reactions between two aldehyde groups) or Schiff-base reactions (i.e., reactions between an aldehyde group and an amino group (See e.g,Nimni et al., "Bioprosthesis derived from crosslinked and chemically modified collagenous tissues," in *Collagen*, vol. 3, M. E. Nimni et al., CRC Press, Inc., Boca Raton, Fla. [1988], p. 5). It may also reduce the interchain disulfide bonds in the helical region of the same molecule, present only in type III collagen (See e.g., D. Amiel et al, "Biochemistry of tendon and ligament," in *Collagen*, vol. 3, p. 229, supra).

Following the second enzyme treatment, the excess water was drained, and the solids were washed three times with 2 liters of deionized water. Although it is not necessary to an understanding of the present invention, it may be that the first enzyme treatment liberates the collagen in the preparation to an extent that is susceptible for further attack by a reducing agent (e.g., sodium sulfide, thiothreitol, dithiothreitol, glutathione or sodium borohydride), with or without alkali compounds to swell the collagen. Following chemical treatment, a second treatment with papain was conducted, in order to thoroughly eliminate all of the residual non-collagenous contaminants (e.g., interstitial elastin).

Collagen prepared according to the two-step enzymatic treatment, as well as collagen prepared with the one-step enzymatic treatment described in Example 1 was tested to determine the degree of removal of non-collagenous fibrous proteins (e.g., elastin) as described in Example 3.

EXAMPLE 3

Insoluble Non-Collagenous Protein (Elastin) Content

In this Example, various samples of collagen preparations were tested for the amount of non-collagenous insoluble protein present, using the methods described by Soskel et al. ( N. T. Soskel et aL, Meth. Enzymol., 144:199 [1952]). The samples tested in this Example were treated as described below.

Briefly, approximately 25 g of wet test sample were delipidated using 2:1 chloroform:methanol (v/v). The samples were frozen in liquid nitrogen and crushed into pieces. The pieces were then placed in 100% isopropyl alcohol to prevent bacterial growth. The pieces were then centrifuged at 5,000×g for 15 min, the supernatants were decanted, and the pellets were air dried at 60° C. The dried samples were then brought to room temperature in a desiccator and the approximately 10 g of each sample were placed in 200 ml polypropylene tubes. One hundred ml of 0.1N NaOH at 4° C., was added to each tube and the contents were mixed. The tubes were then placed into a boiling water bath for 45 minutes. As elastin degradation begins to occur after 60 minutes, it was determined to be important to remove the tubes from the boiling water bath after 45 minutes. The samples were then washed with cold 0.1N NaOH, and then washed with cold double distilled water. The samples were dried over $P_2O_5$ or lyophilized, in order to avoid the inclusion of moisture in the samples that would result in a higher weight measurement. The samples were kept in a desiccator until use. The samples were brought to a constant weight (i.e., the samples were repeatedly weighed until the weight no longer varied) for gravimetric quantification.

In Table 1, the results are shown as percent dry weight from 10 g of dry starting sample. In this Table, results are shown from samples prepared using the "normal" and "robust" papain enzyme treatments (i.e., the robust treatment described in Example 1). In this Table, "Enzyme Only" refers to a sample that processed according to the method described in Example 1 (i.e., it was processed without any reducing agent—the first enzyme treatment was conducted and the treatment process was halted).

In this experiment, samples prepared according to the TTP method described above were tested, as well as samples prepared according to the "Robust Treatment" described in Example 1. In addition, two other samples were tested using both the normal treatment and robust treatments. The "Enzyme→Reducing Agent" sample refers to a sample that was tested following one enzyme treatment and one reduction step (i.e., the first enzyme treatment of Example 2, followed by the reducing step of Example 2).

The sample indicated as "Reducing Agent→Enzyme" refers to sample that was tested following one reduction step followed by one enzyme treatment. This "Reducing Agent→Enzyme" sample was prepared from the same source of collagen, cut, and washed as described in Examples 1 and 2. The test sample was first reduced using the reduction method described in Example 2, but without the first enzyme treatment. Following this reduction step, the methods described for the first enzyme treatment were conducted on the reduced sample.

The sample indicated as "TTP™-Treated" was a sample prepared according to the methods of Example 2. As no insoluble non-collagenous protein was detected using the normal methods of "TTP™-treatment", the robust version of this process was not conducted. The characteristics of this TTP™-treated sample are discussed in more detail in Example 5 below.

The untreated control contained 1.24±0.190 percent dry weight of non-collagenous insoluble protein, while the sample prepared by the TTP process, had no detectable dry weight non-collagenous insoluble protein. These results indicate that there was a significantly greater degree of removal of extraneous non-collagenous proteins in this experiment, as compared to collagen prepared with only one enzyme treatment step, as described in Example 1.

TABLE 1

Non-Collagenous Insoluble Protein Concentration

| Sample | Normal Treatment | Robust Treatment |
|---|---|---|
| Enzyme Only | 0.31 ± 0.020 | 0.27 ± 0.016 |
| Enzyme→Reducing Agent | 0.30 ± 0.027 | 0.25 ± 0.014 |
| Reducing Agent→Enzyme | 0.19 ± 0.013 | 0.21 ± 0.029 |
| TTP™-Treatment | Not Detected | Not Conducted |

EXAMPLE 4

Delipidation of TTP™-Treated Collagen

In this Example, collagen treated with TTP™, as described in Example 2 was delipidated, in order to remove additional potentially immunogenic sites from the TTP™-treated collagen.

Fractional Salt Precipitation First, the TTP™-treated type I collagen was separated by fractional NaCl salt precipitation as described by Hill and Harper (R. J. Hill and E. Harper, Anal. Biochem., 141:83–93 [1984]). Briefly, the enzyme-treated collagen was dissolved in 0.5M NaCl in Tris (hydroxymethyl amino methane buffer), at pH 7.4. The NaCl concentration was then increased to 1.7M. The solution was mixed and centrifuged at 10,000×g for 1 hour at 0°–4° C. The dewatered precipitate was mixed and solubilized in 0.5M acetic acid, and the pH was adjusted to 7.0. Sodium chloride was added to a final concentration of 2.5M, and the precipitate was collected by another centrifugation step as above.

The precipitated collagen was then dialyzed against deionized water and lyophilized prior to delipidation for quantitative analysis of the lipid content in the collagen sample.

In later experiments, it was found that this fractional salt precipitation was often not necessary, as it did not affect the purification level of the TTP™-treated type I collagen protocol. However, it is intended that this step may be conducted prior to delipidation.

Delipidation

The collagen preparation was then dilipidated using the method of Folch et al., (Folch et al, J. Biol. Chem., 226:497–509 [1957]), with modifications. This step involved solvent extraction of total lipids, including gangliosides and phospho-inosities. Briefly, the collagen preparation was stirred in a mixture of chloroform and methanol (2:1, v/v). The volume of the chloroform: methanol was 20 times that of the collagen sample (i.e., 20 parts of the chloroform:methanol mixture were added to 1 part of collagen sample). The sample was stirred well during this addition, and vigorously shaken for one hour at 40°–45° C.

The homogenate was transferred to a vial, and 0.2 volumes of 0.88% KCl were added. The two phases of the mixture were allowed to separate in a separating funnel. The lower phase containing major lipids was removed, and the upper phase, which contained the collagen was washed twice with a mixture of 3:48:47 (v/v) chloroform:methanol:water. The collagen preparation was then washed with a mixture of 5:80:15 (v/v) of the same components (i.e., chloroform:methanol:water), and dewatered using a pressure of 9,000±1000 psi, using a hand press. This squeezed the water from the collagen preparation to produce a dewatered mass. However, it is contemplated that pressures ranging from approximately 8000 psi to 30,000 psi are suitable for use in this step. Application of pressure at 8000 psi removes all of the extraneous water from outside of the molecules, while application of approximately 30,000 psi removes even the intramolecular water. However, it is not intended that the present invention be limited to these specific pressures.

The compressed cake was then dispersed, using a coffee grinder, and air dried in a ventilated drying oven at 40°–45° C. The purity of the delipidated sample was then tested for phospholipids, neutral lipids and glycolipids as described below.

Thin layer chromatography (TLC) was used as described by Skipski et al., (Skipski et al., Biochem. J., 90:374–378 [1964]) to detect phospholipids in the samples. Briefly, 10 g of delipidated sample was tested using a silica gel TLC method. The TLC plate was prepared by first preparing a slurry of 45 g of silica gel H (Spectrum) in 65 ml deionized water. The slurry was poured onto a clean glass plate (20 cm×20 cm), to a thickness of 0.5 mm, air dried and activated (i.e., cured) for 60 minutes, at 60° C., cooled to room temperature, and used immediately. A known quantity of extracted lipid (200 µl) was applied as a streak to the dried silica gel, approximately 2 cm from the bottom of the plate. The sample was allowed to air dry and then was run in an irrigating medium of chloroform:methanol:aqueous ammonia (28%), at a ratio of 65:25:5 (v/v) in a glass chamber. When the solvent front reached near the top of the plate, the plates were removed from the glass chamber and air dried. The plates were then developed with iodine vapor. Yellowish-brown spots appeared at locations where phospholipids were present. Quantification of the phospholipids present was conducted using the methods of Fiske and Subbarow, as described in Example 7, below. The results are shown in Table 2, below.

The presence of neutral lipids and glycolipids in the TTP™-treated collagen was determined using a silicic acid column chromatographic method, as described by Rouser et al. (G. Rouser et al., Lipids 2:37–40 [1967]). Briefly, a column (10 mm×20 mm) containing silicic acid (Spectrum) was prepared and 10 g of the delipidated collagen was applied in sequential portions of 2 grams each, to the column. Thus, the total 10 g sample was divided into five runs on the column; all of the eluted samples were pooled. The sample was eluted with 160 ml of chloroform:acetone (1:1, v/v), followed by a series of acetone and acetone:water solutions. The eluted neutral and glycolipids were collected from the column, air dried. and estimated gravimetrically. The results are shown in Table 2.

For purposes of comparison, multiple samples of the lyophilized collagen samples prepared prior to the delipidation step described above, were subjected to lipid extraction using different organic solvents. Fifteen grams of dry sample were placed in multiple containers. Then, 100 ml of each of solvent was added to each container (i.e., one solvent was added to each sample). The solvents used in this experiment were ether, hexane, methanol, ethanol, isopropyl alcohol, benzene, chloroform, acetone, and chloroform:methanol (2:1). The containers were incubated at approximately 40° C., with agitation using an orbital rotator at 100 rpm, for 6 hours. The solvents were then separated from the collagen samples by centrifugation and evaporated. Ten grams of each delipidated and dried samples treated with the various solvents were used in the lipid estimations as described above. The results are shown in Table 2, below. In this table, the percentages are expressed as the percent of total dry sample weight of collagen.

TABLE 2

Evaluation Of Delipidation Methods

| Delipidation Method | % Phospholipids | % Neutral Lipids And Glycolipids |
| --- | --- | --- |
| Chloroform:Methanol (2:1) | <0.0001 | <0.0001 |
| Ether | 0.0210 | 0.0037 |
| Hexane | 0.0260 | 0.0031 |
| Methanol | 0.0190 | 0.0039 |
| Ethanol | 0.0200 | 0.0030 |
| Isopropyl Alcohol | 0.0190 | 0.0030 |
| Benzene | 0.0230 | 0.0029 |
| Chloroform | 0.0240 | 0.0030 |
| Acetone | 0.0170 | 0.0028 |

As indicated in Table 2, no detectable quantities of phospholipids, neutral lipids, nor glycolipids were detected in the chloroform:methanol extracted samples produced as described above. On the contrary, the same protein samples showed detectable quantities of phospholipids, neutral lipids and/or glycolipids, when the delipidation was done by traditional methods (e.g., using a single solvent system such as ether, hexane, methanol, ethanol, isopropyl alcohol, benzene, chloroform, or acetone). These phospholipids, neutral lipids and/or glycolipids are detectable in these samples even after prolonged extraction (e.g., several days) at room temperature or slightly higher temperatures (e.g., 50° C.).

EXAMPLE 5

Cysteine, Hydroxyproline and Hexosamine And Elastin (Insoluble Non-Collagenous Protein) Content Of TTP™-Treated Collagen In this Example, the cysteine, hydroxyproline, hexosamine, and elastin content of delipidated and TTP™-treated collagen was determined. The hydroxyproline content is recognized as a measure of the amount of collagen present in a sample.

The delipidated and dehydrated type I collagen sample was reconstituted in 0.1M acetic acid, to a concentration of 0.3% (w/v). The purity of the collagen was evaluated by HPLC to determine its amino acid content using a Beckman 6300 amino acid analyzer, according the manufacturer's instructions. The cysteine content of the sample was determined, as was the cysteine content of a collagen preparation that was "less phosphorylated," as described in Example 6. These results indicated that the mole percentage of both the TTP™-treated collagen and "less phosphorylated collagen" was 0.09.

In addition, the insoluble non-collagenous protein (i.e., elastin) content of TTP™-treated collagen was determined using the methods described in Example 3 for testing the insoluble non-collagenous protein content of collagen. As elastin was the only non-collagenous protein potentially remaining in the TTP™-treated type I collagen preparation, it was considered important to determine the elastin content of this preparation, in comparison with collagen treated using other methods (e.g., the phosphorylated collagen of Example 6). The results of these experiments are shown in Table 3, below. These results are expressed as a percentage (wt/wt) on a dry weight basis.

The hydroxyproline and hexosamine contents of the delipidated and dehydrated type I collagen, as well as collagen prepared according to the methods described in U.S. Pat. No. 5,374,539, and two phosphorylated collagen samples ("more phosphorylated" and "less phosphorylated") described in Example 6, were tested in the following experiments.

Determination Of Hydroxyproline Concentration

The hydroxyproline content of the delipidated and dehydrated type I collagen, as well as collagen prepared according to the methods described in U.S. Pat. No. 5,374,539, and two phosphorylated collagen samples ("more phosphorylated" and "less phosphorylated") described in Example 6, were estimated using the method described by Stegeman (H. Stegeman, J. Physiol. Chem., 311:41 [19581]). The 0.03M chloramine T used in this Example was prepared by added 0.845 g chloramine T to 100 ml of a buffer comprised of 20 ml water, 30 ml propanol, and 50 ml citrate-acetate buffer, pH 6. The citrate-acetate buffer (pH 6) was prepared by adding 50 g citric acid (1 $H_2O$ ), 12 ml glacial acetic acid, 120 g sodium acetate (3 $H_2O$ ), and 34 g NaOH to 500 ml water. The volume was adjusted to 1 liter, and the pH was adjusted to 6. Perchloric acid (3M) was prepared in 25.5 ml 70% $HClO_4$, and the volume adjusted to 100 ml in water. The hydroxyproline stock was comprised of 5 μg hydroxyproline per ml water. The hydroxyproline standards were prepared by adding 20 mg hydroxyproline per 100 ml water and 0.05 ml concentrated HCl.

The hydroxyproline concentrations were determined as follows. One ml of each sample and 1 ml of standard solution containing 2–5 μg hydroxyproline were added to 1 ml chloramine solution in separate tubes, and mixed for 20 minutes at room temperature. One ml perchloric acid was then added to the tubes, and mixed at room temperature for 5 minutes. One ml of 5% p-dimethylaminobenzaldehyde in propanol was added to each tube, and mixed for 18 minutes in a 60° C. water bath. The tubes were cooled to 20° C., and optical density was read at 550 nm. The results are shown in Table 3, below.

Determination Of Hexosamine Concentration

The total hexosamine concentration of the delipidated and dehydrated type I collagen, as well as collagen prepared according to the methods described in U.S. Pat. No. 5,374, 539, and two phosphorylated collagen samples ("more phosphorylated" and "less phosphorylated") described in Example 6, were also estimated, using the method described by Blumenkrantz et al (N. Blumenkrantz and G. Absoe-Hansen, Clin. Biochem., 9:269 [1976]).

The trisodium phosphate-potassium tetraborate solution used in this experiment was prepared by mixing 98 ml of 1N tribasic sodium phosphate and 0.5N potassium tetraborate. This trisodium phosphate-potassium tetraborate solution was then used as the solvent for the acetylacetone mixtures for determination of hexosamine in the samples. Acetylacetone I was prepared as a 3.5% (v/v) solution in sodium phosphate-potassium borate buffer. Acetylacetone II was prepared as a 3.5% (v/v) solution in 0.5N potassium tetraborate. The Erlich's reagent used in these Examples was prepared by adding 3.2 g p-dimethylaminobenzaldehyde in 30 ml 12N HCl, diluted with 210 ml 2-propanol.

Briefly, the delipidated sample was placed into a tube, 6N HCl was mixed into the sample, and the sample was allowed to hydrolyze for 30 minutes at 120° C. (or 12–14 hours at 100° C.). The sample was then evaporated to dryness. Concurrently, standards of glucosamine and galactosamine (2.5 to 40 μg for each) were hydrolyzed and evaporated to dryness using the same methods. The samples and standards were resuspended in double distilled water.

In the assay to determine the amount of total hexosamine, 0.8 ml of sample or standard was added to 0.6 ml 3.5% acetylacetone I in separate test tubes, and mixed. The tubes were heated at 100° C. for 30 minutes, and cooled. Then, 2 ml Erlich's reagent was added to each tube and mixed. The tubes were incubated for 5 minutes and the optical density at 535 nm was determined.

In the assay to differentiate between glucosamine and galactosamine, 0.8 ml of sample or standard was added to 0.6 ml 3.5% acetylacetone II in separate test tubes, and mixed. The tubes were allowed to sit for 2 hours in crushed ice, followed by heating at 50° C. for 15 minutes. Then, 2 ml Erlich's reagent were added to the tubes and mixed. The tubes were incubated at room temperature for 30 minutes and the optical density at 530 nm was determined. The results are shown in Table 3, below. The results are shown as a percentage (wt/wt) on a dry weight basis.

TABLE 3

Elastin, Hydroxyproline And Hexosamine Concentration Determinations

| Sample | Elastin (% wt/wt) | Hydroxyproline (% wt/wt) | Hexosamine (% wt/wt) |
| --- | --- | --- | --- |
| Raw, Untreated Bovine Tissue Control | 0.95 | 3.27 | 1.24 |
| TTP™-Treated Bovine Collagen | Not Detected | 9.83 | Not Detected |
| U.S. Pat. No. 5,374,539 Collagen | 0.02 | 9.45 | Not Conducted |
| Less Phosphorylated Collagen | Not Detected | 9.76 | Not Detected |
| More Phosphorylated Collagen | Not Detected | 9.75 | Not Detected |

EXAMPLE 6

Chemical Modification of Filter-Sterilized Collagen Type I

In this Example, TTP™-treated collagen prepared according to the methods described in Example 5 were further treated to produce "CollagenPRO™." Thus, as it is used in the present invention, "CollagenPRO™" refers to purified collagen that has been phosphorylated.

CollagenPRO™ was prepared from TTP™-treated collagen prepared according to the methods described in Example 5. First, TTP™-treated collagen was filter sterilized by passing the preparations through a 0.22 μ filter attached to a 30 ml syringe. The filter-sterilized collagen suspensions were then stored until use at 4° C. These filter-sterilized collagen preparations were chemically modified in order to determine the optimum modifications for production of purified collagen suitable for biomedical applications. The entire procedure was conducted under sterile conditions, using pre-sterilized ingredients and pyrogen-free, sterile water.

First, 100 ml of a 0.3% solution of collagen in 0.1M acetic acid was treated with 5N NaOH at 4° C., until the pH reached 11.5. Then, sodium trimetaphosphate was added to a final concentration of 0.03M. The collagen was allowed to react in a sterile hood kept at room temperature for approximately 3 hours with agitation using an orbital rotator, at 160 rpm. This modified collagen was washed by dialysis against deionized water at 4° C., until no residual ions leached out of the collagen sample. Portions of the modified collagen were dried by lyophilization (i.e., freeze-drying) using methods commonly known to those in the art. The lyophilized samples were stored in a desiccator for a minimum of five days prior to additional testing.

For some experiments, it was of interest to include purified collagen with a varying degrees of phosphorylation. For samples with more phosphorylated collagen, referred to as "More Phosphorylated Collagen" in the accompanying Examples, approximately 40% of the modifiable sites available in the collagen were phosphorylated. For samples with lesser degree of phosphorylation; this preparation is referred to as "Less Phosphorylated Collagen" in the accompanying Examples. To achieve a purified collagen with less phosphorylation, 0.01M sodium trimetaphosphate was used in the phosphorylation step, rather than 0.03M sodium trimetaphosphate. In addition, the incubation period was 1 hour, rather than the 3 hours used with 0.03M sodium trimetaphosphate.

It is contemplated that phosphorylation of biomolecules, such as growth factors (e.g., EGF), interleukins (e.g., IL1), and other biologically active molecules is beneficial. For phosphorylation of EGF, 1 ml of 0.1% EGF adjusted to pH 11.5, is added to 0.2 ml sodium trimetaphosphate, at the same concentrations and conditions (e.g., agitation and temperature), as described above. The sample is then dialyzed to remove salts, and the phosphorylated EGF may be used as appropriate. EXAMPLE 7

Testing For Covalently-Bound Phosphorous

In this Example, washed collagen sample was tested for the presence of covalently bound phosphorous, using the procedure described by Fiske and Subbarow (C. H. Fiske and Y. Subbarow, J. Biol. Chem., 66:375–400 [1925]). Briefly, 1 mg of dry modified collagen prepared and lyophilized according to Example 6 was mixed with 1 ml of 72% perchloric acid, and then digested at 200° C., for 20 minutes. Deionized water was added to the digested sample to adjust the volume to 4 ml. Then, the following reagents were added in succession, and mixed well. First, 0.4 ml of 2.5% ammonium molybdate in 3N sulfuric acid was added. To this mixture, 0.2 ml of the reducing agent, 1-amino-2-naphthol sulfonic acid was added. The collagen mixture was then incubated for 10 minutes at 100° C., and observed for the development of color, as measured at 600 nm in a spectrophotometer (Beckman DU-2). Potassium dihydrogen monophosphate was used as a phosphorous standard. Unmodified collagen prepared according to Example 2 was used as a control.

The phosphorous content was estimated by graphing the results obtained with the potassium dihydrogen monophosphate standards. In this experiment, no bound phosphorous was detected in the TTP™-treated samples. For samples with more phosphorylated collagen (i.e., where 40% of the modifiable sites available in the collagen were phosphorylated), 2.5% (wt/wt; dry weight basis) bound phosphorous was detected. For samples with less phosphorylation, 0.8% (wt/wt; dry weight basis) bound phosphorous was detected.

Figure 2:
FIG. 2 is a schematic showing phosphorylation of serine to phosphoserine.
Figure 2:
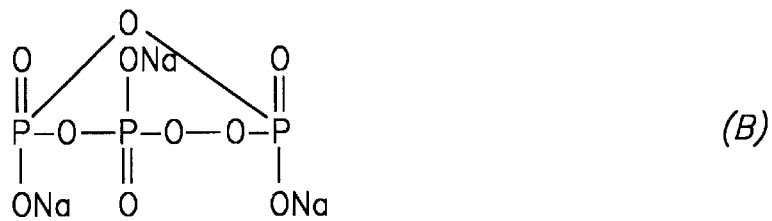
Figure 2:
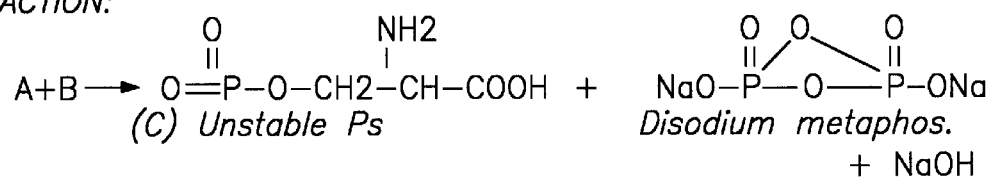
Figure 2:
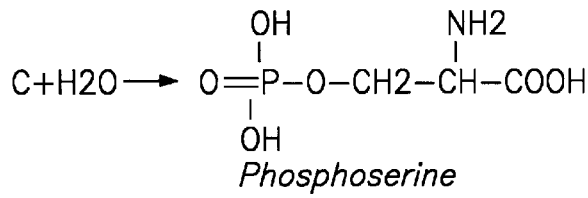

These results indicated that there was a significant increase in the phosphorous content of the modified collagen as compared to the untreated control. No measurable amount of phosphorus was detected in the untreated collagen control sample. It was estimated that a considerable number of hydroxy amino acids (e.g., serine and tyrosine) were irreversibly phosphorylated to form phosphoester bonds. Although it is not necessary to understand the invention, FIG. 2 shows a reaction that may occur during this phosphorylation.

This modified collagen was shown to possess improved biological characteristics, as described in Examples 10–15. However, it is recognized that care must be taken in the purification of collagen, as impurities present in impure collagen preparations may engender unfavorable biological reactions due to the phosphorylation of contaminant proteins (e.g., elastin).

Importantly, the amount of modification can be controlled, ranging from none to a maximum of approximately 40% of the modifiable amino acids present in collagen. The pH conditions under which the reaction occurs may vary from 8 to 13, depending upon the amount of modification desired. In addition, the reaction temperature may range from 4°–45° C. It was observed in other experiments, that the samples tend to freeze at temperatures less than 4° C., while at temperatures above 45° C., the collagen may become denatured.

The chemical used to react with the collagen may be selected from the group comprising, but not limited to, various polyphosphates (e.g., sodium hexametaphosphate, sodium ultraphosphate, and sodium tetrametaphosphate), phosphoric anhydride, and phosphoryl trichloride solubilized in organic non-polar solvents such as hexane, etc.

It is also contemplated that other non-collagenous biological materials for various biological applications will be chemically modified in a like manner. It is also contemplated that other modifications useful for preparing collagen to be used in cell culture or in vivo applications, including, but not limited to fluorination, halogenation (e.g., chlorination), sulfonation, and/or hydroxylation may be performed on collagen prepared according to the methods of Example 2, as well as phosphorylated collagen prepared according to the above described methods. It is contemplated that these modifications be conducted in conjunction (i.e., multiple modification procedures may be conducted on the same preparation), as well as separately. EXAMPLE 8

Solubility of Modified Collagen

In this Example, the solubility of purified type I collagen, modified as described in Example 6 was determined, and compared with the solubility of native collagen.

In this Example, 10 ml of 0.3% solutions of unmodified (i.e., native) collagen and modified collagen were prepared in 0.1M acetic acid. The optical density of each solution was determined at 450 nm. A small quantity of 0.5M NaOH was carefully added to each solution, in order to adjust the pH to neutrality (i.e., 7). The optical density was again measured at 450 nm. The following table shows the optical density values for these samples. The increase in optical density of the native collagen indicated that there was more insoluble protein in this sample, as compared to the modified collagen. Thus, the modified collagen was also found to have better solubility features under neutral conditions. While it is not necessary to understand the present invention, this observation may be the result of a shift in the isoelectric point of the collagen.

TABLE 4

Solubility Of Modified And Unmodified Collagen At pH 3.5 And 7

| Sample | Optical Density At pH 3.5 | Optical Density At pH 7 |
| --- | --- | --- |
| Unmodified Collagen | 0.001 | 0.06 |
| Modified Collagen | 0.001 | 0.01 |

EXAMPLE 9

Preparation of ColiagenPRO™ Film

In this Example, films (i.e., membranes) of chemically-treated, filter-sterilized collagen (i.e., CollagenPRO™), prepared according to the methods described in Example 6 were prepared for use in in vivo and in vitro experiments. In some experiments, the collagen was prepared from bovine Achilles tendons, rather than bovine hide. Both collagen sources were found to be satisfactory for use in the following Examples.

First, the suspension was poured into sterile 15×2 cm petri dishes to a depth of approximately 8 mm. The petri dishes were covered, and stored at a constant temperature of 37° C. for 48 hours, in order to promote uniform initial gelation. This often required 3–5 days for the films to visually appear to be dry. At the end of the 48 hour initial gelation phase, the petri dishes were uncovered, and drying was allowed to continue at room temperature in a chemical fume hood. At the end of drying, the collagen films were sterilized with ethylene oxide gas and used for animal implantation, transplantation, grafting, or other experiments. These films were also used in subsequent experiments.

EXAMPLE 10

In Vivo Evaluation of Chemically Modified Collagen In Skin Transplants

In this Example, the suitability and biocompatibility for in vivo applications of the chemically-modified collagen type I produced as described in Example 6, unmodified collagen prepared as described in Example 2, were determined. Purified, washed collagen samples obtained as described in Example 9, were dried in the form of thin films of 0.3 mm thickness.

In this Example, sixteen adult male Swiss albino mice were used to test the suitability and biocompatibility of these collagen preparations. First, a circular area of 1 cm in diameter of skin was surgically removed from the backs of the animals. These areas were then covered under aseptic conditions with test or control collagen film (i.e., grafted). The collagen used in this Example was sterilized by exposure to ethylene oxide. The animals were observed for gross indications of inflammation (i.e., redness, swelling, heat, etc.), for a three week period. No adverse responses were noticed for any of the animals. The animals were then sacrificed at the end of three weeks following the grafting of the collagen film.

The entire skin flap, including the grafted collagen was removed from each of the animals from the surgical site, and fixed in 70% alcohol, dehydrated, and embedded in wax, using methods known in the art. Embedded samples were cut into sections 5 microns in thickness, and stained with Goldner's one-step trichrome stain (OST), and hematoxylin and eosin (H & E), using methods known in the art.

The histological results showed no adverse response with either of the two experimental groups. Cellular infiltration and the rate of neo-epithelialization (i.e., epithelial cell infiltration towards the center of the graft) was not affected by any of the test graft materials. In contrast, the control sample showed noticeable numbers of foreign body giant cells attached to the collagen film. In addition, as shown in FIG. 2, there was a slower rate of epithelialization observed in the controls.

EXAMPLE 11

In Vivo Evaluation of Chemically Modified Collagen In Implants

In this Example, type I collagen obtained from tissue samples of bovine intestine (obtained from a local market) was purified and chemically modified using the methods of Example 6. These samples were then implanted into rabbits, in order to determine the suitability and biocompatibility of collagen prepared according to the methods of the present invention. In these experiments, control collagen prepared according to the methods described in Example 2 was also used.

Adult, male New Zealand white rabbits of approximately 3.5 to 4 kg obtained from the Nitabell Rabittry were used in this Example. The animals were first sedated with an appropriate dosage of ketamine, and anesthetized with ketamine/ xylaxine (PDL) as appropriate for minor surgery. The hair on the dorsal side of the animals was shaved and prepared for surgery with a betadine scrub and a 70% alcohol wipe. The animals were divided into three groups of two animals each. A small incision was made in the skin of each animal, in order to create subcutaneous pockets. Four implantations were made for each group of rabbits. Six of the rabbits (24 sites) were operated on bilaterally, with implants placed on both sides of the dorsal mid-line. Each implant comprised 50 mg of dried collagen sample were rolled into an approximately round ball and placed subcutaneously at each site.

The animals were observed for three weeks for gross indications of inflammation (e.g., redness, swelling, etc.). No adverse responses were observed for any of the animals. After 3 weeks, the animals were sacrificed and the implants were surgically removed, fixed in 70% alcohol, dehydrated and embedded in paraffin, using methods commonly known in the art. Sections of 5 micron in thickness were cut, and stained with OST and H & E, using methods commonly known in the art.

The results showed more vascularization and fibroblastic ingrowth in both experimental groups. The control samples had relatively poor vascularization, as well as a prevalence of multi-nucleated giant cells, reflecting the lesser biocompatibility of these samples.

EXAMPLE 12

Alkaline Phosphatase Activity

In this Example, the collagen implants tested as described in Example 9 were analyzed for their alkaline phosphatase activity. Alkaline phosphatase activity was of interest, as it has been hypothesized that this enzyme is involved in tissue formation and calcification. The assay used in this Example is based on the methods of Bradenberger and Hanson (H. Bradenberger and R. Hanson, Helv. Chim. Acta 36:900 [1953]; and Hofstee (B. H. Hofstee, Arch. Biochem. Biophys., 51:139 [1954]). In this calorimetric method, the effect of alkaline phosphatase on the hydrolysis of o-carboxy-phenyl phosphate is measured.

Briefly, samples of approximately 10 mg from each of the harvested collagen implants from Example 10 were dispersed at a rate of 1 mg in 1 ml of Tris buffer (0.1M Tris, pH 8.5) for five minutes. Care was taken to maintain the temperature of the dispersed samples at 0°–5° C., in order to prevent enzymatic reactions from occurring prior to the assay procedure. A small amount of detergent (to a final concentration of 0.1M sodium deoxycholate) was added to the dispersed samples, in order to facilitate the release of membrane-bound enzymes. The dispersed samples were then mixed in a Polytron homogenizer (Brinkmann), for 30 seconds, while they were chilled in an ice bath.

For each sample, the solutions were incubated in a water bath at 25° C., for 20–30 minutes in order to allow activation of the enzymes. A test solution comprised of 2 ml glycine (0.2M, pH 8.8), 1 ml of 3.65 mM o-carboxy phenyl phosphate (OCCP), and 0.5 ml of 0.05M $MgCl_2$ was placed into a cuvette, and allowed to incubate for 3–4 minutes at 25° C. Collagen test samples (0.1 ml, prefiltered using a 0.22 micron filter attached to a 5 ml syringe) were added to the solutions in the cuvettes. The optical density of the cuvette contents was then determined at 300 nm, at room temperature.

The activity is expressed in units per mg of tissue, as based on the number of micromoles of OCCP hydrolyzed per minute at 25° C., at pH, under the conditions described above.

The results showed significantly elevated amounts of alkaline phosphatase (34% increase; $p<0.0005$) activity in the modified collagen implants as compared to the unmodified implants.

EXAMPLE 13

Use of CollagenPRO™ For Wound Healing

In this Example, the suitability of type I collagen was extracted from bovine Achilles tendons (obtained from a local market), and made into uniformly thin dry films as described in Example 9. A control film was prepared using the standard pepsin enzyme treatment method described in U.S. Pat. No. 5,374,539, herein incorporated by reference. In addition to the Collagen PRO™ described in Example 9, native type I bovine collagen prepared as described in U.S. Pat. No. 5,374,539, and bovine collagen cross-linked with glutaraldehyde (as described in this patent), were tested. All of these samples were tested without in the presence of 0.5 ml of reconstituted epidermal growth factor (EGF; Collaborative Research Inc.)(1 µg/3 ml PBS), as well as without the addition of EGF.

Epithelial cell cultures were chosen for this Example, as they provide a model system for investigating the events that govern the closure of superficial epithelial defects and for assaying the actions of exogenous agents on these events. These methods provide some advantages, as compared to in vivo models of wound closure. For example, it is much easier to manipulate the extracellular milieu in cell culture systems. Prior reports indicate that the in vitro epithelial response is similar to the response observed in vivo, and can be readily quantified (See e.g. S. Gunasekaran et al., Proc. Soc. Biomater., 20:311 [1994]; and S. Simmons et al., Toxicol. Appl. Pharmacol., 88:13–23 [1987]). This experiment was designed to demonstrate the comparative suitability of various collagen substrata for wound closure. In particular, the interaction of the collagen substrata and EGF were investigated.

Primary cell cultures were established from surgically removed corneas obtained from sacrificed New Zealand white rabbits (1.5–2.5 kg). The surgically isolated corneas were incubated in Dispase II (Boehringer Mannheim) at 37° C., in a humidified $CO_2$ incubator. After 1 hour, the corneas were transferred to primary cell culture medium comprised of Dulbecco's modified Eagle's medium enriched with 5% fetal calf serum, 0.5% dimethyl sulfoxide (DMSO), 50 ng/ml gentamicin, 146 µg/ml L-glutamine, 5 µg/ml insulin, and 10 µg/ml EGF. The full thickness of the corneal epithelial sheets were gently peeled off the corneal samples and placed in trypsin, gently mixed, and centrifuged at 2,000×g for 5 minutes at 4° C. The supernatants were removed and the cells from six corneas were combined and resuspended in fresh primary culture medium and plated in six 35 mm culture dishes. The cultures were placed at 37° C., in a humidified $CO_2$ incubator. The culture medium was changed three times per week.

By day 7 of incubation, the primary cultures had grown to confluency and were trypsinized for 5–10 minutes. The cells were pipetted from the culture dishes and centrifuged at 2000 xg for 5 minutes. The supernatant were removed and the control culture medium composed of the Dulbecco's modified Eagle's medium described above, but exclusive of the EGF. The cells were pipetted to yield a suspension of single cells and counted using a hemacytometer. Twenty-four well multiplates were seeded at 3–4×10$^4$ cells/well in 1 ml medium per well. The subcultured cells were grown for 7 days, with the medium changed three times during this period.

On day 7 of subculture, the cells contained in four wells were counted, in order to ensure that each well had at least 1.6×10$^5$ cells. The cell layers were injured ("wounded") using filter disks (7 mm diameter), as described by Jumblatt and Neufeld (See, M. Jumblatt and A. Neufeld, Invest. Ophthamol. Visual Sci., 15:4–14 [1986]). Briefly, the cell culture medium was removed from the wells and the filters were placed on top of the cell layer and pressed down with a plunger (7 mm diameter). A pre-chilled steel probe 6 mm in diameter was held for 5 second on the bottom of the wells, directly below each disk. Disks with adherent dead cells were then removed from each well. Prior to adding the control medium, the test materials (collagen prepared according to the methods described in Example 9 (CollagenPro™), as well as native type I bovine collagen and cross-linked type I bovine collagen (prepared according to U.S. Pat. No. 5,374,539), were added to each well. The multiplates containing the "wounded" cell layers and test collagens were re-incubated for 24 hours, to allow the growth of cells into the wounded area. The wells were observed at intervals during this 24 hour growth period, to measure the area of cell layer wounded by the disk. These measurements were taken microscopically, at 0. 12, 18, and 24 hour time intervals.

Closure of the injured area on the cell layer within the wells was stopped by fixation of the cell layers and collagen test samples, with 10% neutral buffered formalin, for at least 10 minutes. The cells were then stained with Giemsa stock solution for at least 10 minutes, rinsed in 10% neutral buffered formalin, and allowed to air dry. The stained wells contained in the microplate were observed microscopically and the wound areas were measured.

Figure 3:
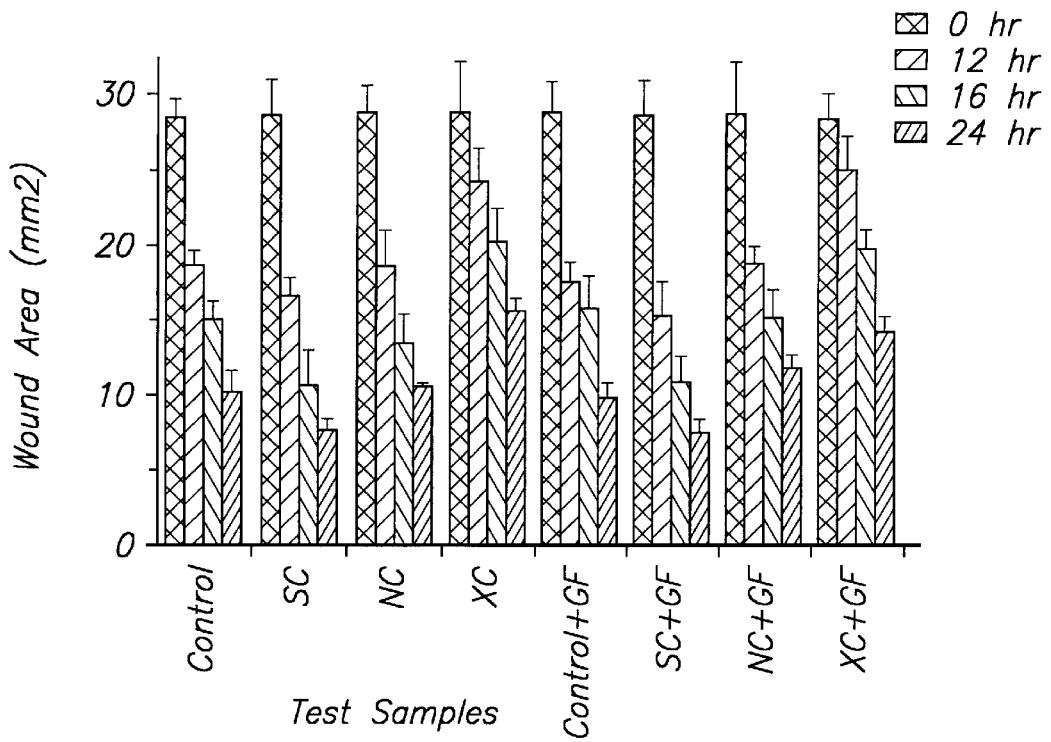
FIG. 3 is a bar chart showing the wound healing properties of various collagen preparations.

FIG. 3 is a bar chart that shows the in vitro wound closure results obtained in this Example. In this Figure, "SC" represents CollagenPro™, "NC" represents native collagen, "XC" indicates cross-linked type I bovine collagen, and "GF" indicates EGF. These results indicate that the collagen preparations do not perform in the same manner. The CollagenPro™ with and without EGF results showed a faster wound closure rate compared to the results obtained with the other collagen preparations. The in vivo experiments described in Examples 10 and 11, demonstrated that the delivery of growth factors was more effective when delivered through CollagenPro™, as compared to native type I collagen prepared according to the method of U.S. Pat. No. 5,374,539. In addition, these results indicated that in general, cross-linking of collagen does not assist epithelization.

EXAMPLE 14

In Vitro Hemostatic Tests

In this Example, collagen prepared as described in Example 6, was used in additional tests to determine its utility in in vivo as a hemostatic agent.

Hemostasis (i.e., blood clotting) is a primary event during the steps involved in normal wound repair. Collagen is a natural hemostatic agent that is present in almost every tissue, and which also appears to have specific affinity for cells and growth factors essential for normal wound healing. (See e.g., Gunasekaran, in *Encyclopedia of Biomaterials and Bioengineering*, 2(37):2293–2310 [1995]). Although other materials may assist hemostasis, it is possible that, unlike collagen, they will not optimize the rate of wound healing. The object of this Example was to determine the hemostatic and wound healing abilities of various compounds and substances. In this Example, collagen fibers (Avitene, obtained from Medchem Products), sponges (Helistat, obtained from Collatek), and gelatin (Gelfoam, obtained from Arizona Health Sciences), and gelatin fragments prepared as described below were tested. Additional substances previously used as hemostatic agents, such as thrombin (e.g., Thrombinar and Thromostat), and cellulose (e.g., Surgicel and Oxycel, J & J Medical) were not included in these experiments. Thrombin was not included as it may have immunological and local delivery problems.

Native type I bovine collagen was prepared as described in Example 2. Avitene, Helistat, and Gelfoam were purchased from their respective suppliers. Gelatin fragments were prepared by limited, non-specific protease treatment of gelatin (Sigma). The gelatin fragments were then purified by size exclusion column chromatography on Sephadex G-50 and G-100 gels in Multi-Spin columns (Axygen), as described by the manufacturer. Two groups of fragments were isolated and purified. One group was designated as "high molecular weight gelatin peptide." This group contained peptides of molecular weights in the range of 50–100 kD. The other fragment group was designated "low molecular weight gelatin peptide." This group contained peptides with molecular weights in the range of 30–50 kD.

The standard Lee-White clotting method was used in this Example, as described by Brown (B. A. Brown, *Hematology: Principles and Practice*, 3d ed., Lea & Febiger, Philadelphia, [1980], pgs 125–126), commonly known to those in the hematology art. Multiple experiments were conducted using this method, in which the volume of blood tested was either 0.5 ml or 1 ml (and the other reagents maintained in the proper proportions). As no differences were observed between the tests run with these differing volumes, in most experiments, 0.5 ml blood was used. Briefly, 3 mg of each sample previously stored in a desiccator was carefully measured, and each was separately placed into 10 cm long clean polypropylene vials. Fresh blood (5 ml) obtained by venipuncture from healthy humans was collected, and the time of blood collection was noted. To each tube, 0.5 ml of blood was added and gently agitated every 30 seconds, until clots formed. The time of initial clot formation was noted.

Figure 4:
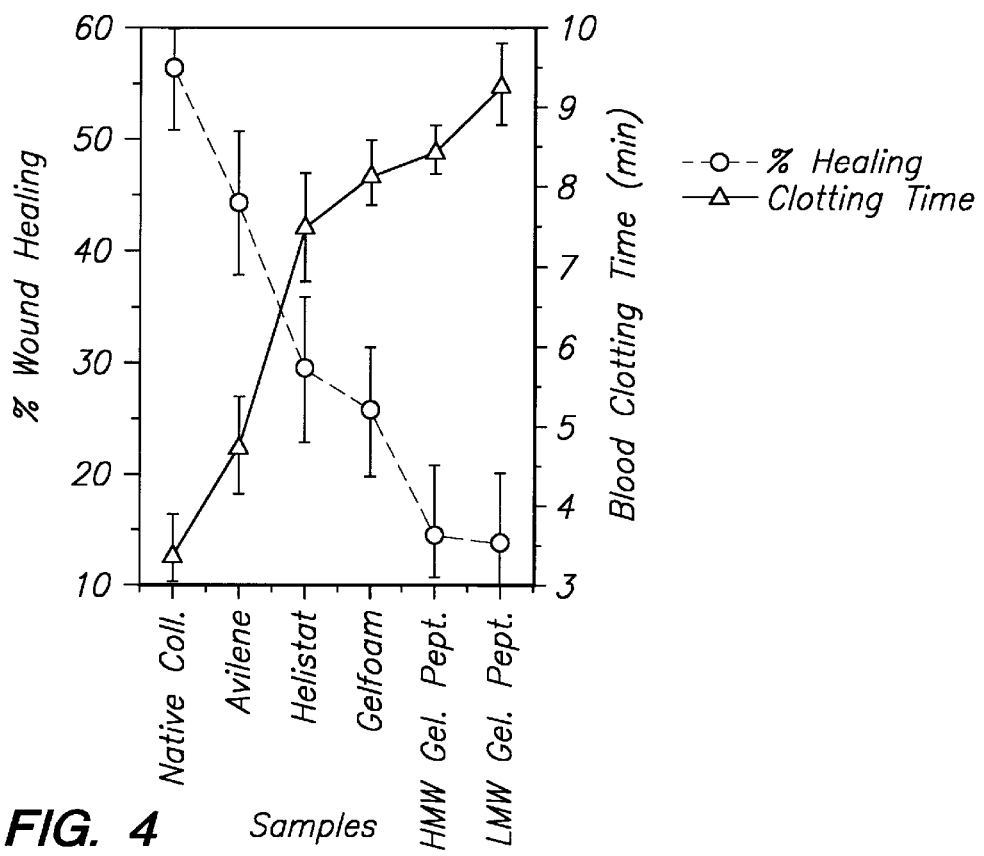
FIG. 4 is a graph showing the wound healing properties and blood clotting times of various preparations.

The results of these experiments are shown in FIG. 4. As shown in this figure, the clotting time was the greatest for the low molecular weight gelatin peptide fragments ("LMW Gel. Pept."), and lowest for the CollagenPro™(indicated as "native coll." in this Figure). The high molecular weight gelatin peptide fragments ("HMW Gel. Pept.") time was almost as high as the low molecular weight gelatin peptides. The collagen fibers obtained from Avitene ("Avitene") had the second-most rapid clotting time, while the Helistat ("Helistat") and Gelfoam ("Gelfoam") preparations had the next most rapid times, respectively. As shown in FIG. 4, the Gelfoam clotting time was only slightly faster than the high molecular weight gelatin peptide fragments.

EXAMPLE 15

Hemostasis In Vivo

This Example, a continuation of the previous example, was conducted in order to assess the hemostatic capabilities of the collagen and other preparations used in Example 9 in vivo.

In this Example, adult male Sprague-Dawley rats were used. Circular regions (2 cm) of full-thickness skin were surgically removed from the backs of anesthetized the animals, as described in Example 10. The exposed areas were aseptically covered with the collagen preparations (i.e., grafted) described in Example 13. After 3 weeks, the animals were sacrificed and the grafts were surgically removed, fixed in 70% alcohol, dehydrated and embedded in paraffin, using methods commonly known in the art. Sections of 5 micron in thickness were cut, and stained with OST and H & E, using methods commonly known in the art.

The relative extent of neo-epithelization and wound healing were observed and assessed histologically. There were no gross signs of inflammation apparent in or around the grafted areas on the animals'backs. The results of this experiment are shown in FIG. 4. As indicated in this figure, the CollagenPRO™ film showed a significantly faster wound healing rate and blood clotting time, as compared to the rest of the samples, with Avitene showing the second fastest rates, and Helistat showing the third fastest rate. The percentage of wound healing and blood clotting time results are shown in FIG. 4.

As previously described, these differing substances provide varying results in biological systems. Although it is not necessary to understand the invention, the relatively poor performance of gelatin and gelatin peptides may indicate that the structure of collagen is important in the processes of hemostasis and wound healing.

From the above, it is clear that the various embodiments of collagen prepared according to the methods of the present invention are suitable for various biomedical applications that require non-inflammatory collagen. It is contemplated that the non-inflammatory collagen of the present invention be used in multiple settings and for numerous applications, including but not limited to, non-inflammatory collagen sutures, collagen soft tissue replacements including wound and burn coverings, arterial vessel replacements, hemostatic agents, drug delivery matrices, vitreous replacement for ophthalmologic therapy, endodontic therapy, cell culture supports, etc. It is further contemplated that various embodiments of the present invention will find use in any form, including, but not limited to fibrous or membrane films, bags, sponges, suture threads, and aqueous suspensions, as well as composite materials. In addition, collagen prepared according to the present invention may be further modified as necessary for the desired application and to provide an improved bioactive response. It is also contemplated that the methods of the present invention will be applicable to the preparation of other biomolecules as well as collagen.

What is claimed is:

1. A method for purifying collagen comprising:
    a) providing:
        i) a sample comprising collagen,
        ii) first and second proteolytic enzyme preparations, wherein both said first and second proteolytic enzyme preparations comprise papain, and
        iii) a reducing agent, wherein said reducing agent is selected from the group consisting of sodium sulfide, dithiothreitol, glutathionine, and sodium borohydride;
    b) exposing said collagen sample to said first proteolytic enzyme preparation comprising papain to produce a first collagen solution;
    c) exposing said first collagen solution to said reducing agent to produce a second collagen solution; and
    d) exposing said second collagen solution to said second proteolytic enzyme preparation comprising papain to produce purified collagen.

2. The method of claim 1, wherein said reducing agent further comprises an alkali selected from the group consisting of sodium hydroxide, ammonium hydroxide, potassium hydroxide, and calcium hydroxide.

3. The method of claim 1, further comprising the step of e) exposing said purified collagen to a delipidation agent to produce dilipidated collagen.

4. The method of claim 3, wherein said delipidation agent comprises a mixture comprising chloroform and methanol.

5. The method of claim 4, further comprising the steps of f) compressing said delipidated collagen to produce compressed collagen; g) dehydrating said compressed collagen to produce dehydrated collagen; and h) dispersing and drying said dehydrating collagen to form collagen fibers.

6. A The method of claim 1, further comprising the step of de-epithelializing said sample prior to exposing said sample to said first proteolytic enzyme preparation.

7. Purified collagen prepared according to the method of claim 1.

8. A method of achieving hemostasis comprising:
    a) providing:
        i) the purified collagen of claim 1, and
        ii) a bleeding wound; and
    b) contacting said bleeding wound with said purified collagen, under conditions such that hemostasis occurs.

9. A method of transplantation comprising:
    a) providing:
        i) the purified collagen of claim 1, and
        ii) a transplantation site; and
    b) contacting said transplantation with said purified collagen, under conditions such that said purified collagen of claim 1 is transplanted to said transplantation site.

10. A method for production of biocompatible collagen comprising:
    a) providing:
        i) a sample comprising collagen,
        ii) first and second proteolytic enzyme preparations, both of which comprise papain,
        iii) a reducing agent, wherein said reducing agent is selected from the group consisting of sodium sulfide, dithiothreitol, glutathionine and sodium borohydride,
        iv) a delipidation agent, and
        v) a phosphorylation agent;
    b) exposing said collagen sample to said first proteolytic enzyme preparation comprising papain to produce a first collagen solution;
    c) exposing said first collagen solution to said reducing agent to produce a second collagen solution;
    d) exposing said second collagen solution to said second proteolytic enzyme preparation comprising papain to produce a proteolyzed collagen solution;
    e) exposing said proteolyzed collagen solution to said delipidation agent to produce delipidated collagen; and
    f) exposing said delipidated collagen to said phosphorylation agent to produce phosphorylated collagen.

11. The method of claim 10, wherein said delipidation agent comprises a mixture of chloroform and methanol.

12. The method of claim 10, wherein said phosphorylation agent is selected from the group consisting of sodium trimetaphosphate, sodium hexametaphosphate, sodium ultraphosphate, sodium tetrametaphosphate, phosphoric anhydride, and phosphoryl trichloride.

13. The method of claim 12, wherein said phosphorylation agent comprises sodium trimetaphosphate.

14. The method of claim 10, further comprising the step of filter-sterilizing said delipidated collagen prior to exposing said delipidated collagen to said phosphorylation agent to produce phosphorylated collagen.

15. The method of claim 10, further comprising the steps of compressing said delipidated collagen to produce compressed collagen; dehydrating said compressed collagen to produce dehydrated collagen; and dispersing and drying said dehydrating collagen to form collagen fibers, prior to phosphorylating said delipidated collagen.

16. Biocompatible collagen prepared according to the method of claim 10.

* * * * *

UNITED STATES PATENT AND TRADEMARK OFFICE
CERTIFICATE OF CORRECTION

PATENT NO. : 5,814,328
DATED : 09/29/98
INVENTOR(S) : Subramanian Gunasekaran

It is certified that error appears in the above-indentified patent and that said Letters Patent is hereby corrected as shown below:

Column 17, line 20, please insert a hard return after the word "Precipitation", such that the phrase "Fractional Salt Precipitation" are the only words on that line.

Column 22, line 19, please insert a hard return after "appropriate.", such that "EXAMPLE 7" is now on the next line by itself.

Column 23, line 29, please insert a hard return after "separately.", such that EXAMPLE 8" is now on the next line by itself.

Column 30, line 31 (Claim 9 b) ), please insert --site-- after the word "transplantation".

Signed and Sealed this

Ninth Day of March, 1999

*Attest:*

*Attesting Officer*

Q. TODD DICKINSON

Acting Commissioner of Patents and Trademarks